United States Patent
Hayashizaki et al.

[11] Patent Number: 5,977,025
[45] Date of Patent: Nov. 2, 1999

[54] 1,3-OXAZIN-4-ONE DERIVATIVE, HERBICIDE CONTAINING SAME, AND INTERMEDIATE FOR PREPARING SAME

[75] Inventors: Keiichi Hayashizaki, Inashiki-gun; Yoshihiro Usui, Ryugasaki; Koichi Araki, Inashiki-gun; Norishige Toshima, Inashiki-gun; Tetsuya Murata, Inashiki-gun; Takako Aoki, Tsuchiura; Atsushi Go, Ushiku; Hideshi Mukaida, Kitasouma-gun; Rika Higurashi, Narita, all of Japan

[73] Assignee: Mitsubishi Chemical Corporation, Tokyo, Japan

[21] Appl. No.: 08/663,118

[22] PCT Filed: Dec. 20, 1994

[86] PCT No.: PCT/JP94/02152

§ 371 Date: Jun. 20, 1996

§ 102(e) Date: Jun. 20, 1996

[87] PCT Pub. No.: WO95/18113

PCT Pub. Date: Jul. 6, 1995

[30] Foreign Application Priority Data

Dec. 24, 1993 [JP] Japan .................. 5-326733

[51] Int. Cl.[6] .................. A01N 43/32; C07D 265/06; C07C 229/12

[52] U.S. Cl. .................. 504/130; 504/223; 544/97; 560/168

[58] Field of Search .................. 544/97; 504/130, 504/223; 560/168

[56] References Cited

U.S. PATENT DOCUMENTS 3,718,688  2/1973  Davis ......................... 560/168

5,696,054  12/1997  Go et al. ..................... 544/97

FOREIGN PATENT DOCUMENTS 372586   6/1990  European Pat. Off. .
557691   9/1993  European Pat. Off. .
93/15064 8/1993  WIPO .

*Primary Examiner*—Richard L. Raymond
*Attorney, Agent, or Firm*—Oblon, Spivak, McClelland, Maier & Neustadt, P.C.

[57] ABSTRACT

This invention provides 1,3-oxazin-4-one derivatives represented by following general formula (I):

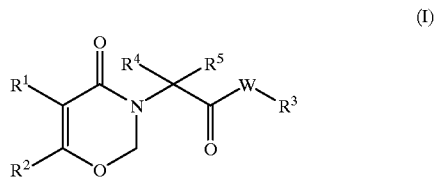

in which $R^1$ represents a phenyl group which may be substituted; $R^2$ represents a hydrogen atom or a lower alkyl group; $R^3$ represents a hydrogen atom, a lower alkyl group, an aralkyl group or a phenyl group which may be substituted; $R^4$ and $R^5$ each independently represent a lower alkyl group; and W represents an oxygen atom or a group represented by the formula $-N(R^6)-$ in which $R^6$ represents a hydrogen atom, a lower alkyl group, a lower alkenyl group or a lower alkynyl group. There are also provided herbicidal compositions containing the derivatives and intermediates for preparing them. The compounds according to the present invention exhibit strong herbicidal activities and thus they are useful as active ingredients of agricultural chemicals.

23 Claims, No Drawings

1

1,3-OXAZIN-4-ONE DERIVATIVE, HERBICIDE CONTAINING SAME, AND INTERMEDIATE FOR PREPARING SAME

The present application is a 371 of PCT/JP94/02152, filed Dec. 20, 1994.

BACKGROUND OF THE INVENTION

1. Field of the Invention

This invention relates to novel 1,3-oxazin-4-one derivatives, herbicidal compositions containing same, and novel intermediates for preparing same.

2. Description of the Related Art

Certain types of 1,3-oxazin-4-one derivatives, such as 6-methyl-3-(1-methyl-1-phenylethyl)-5-phenyl-2,3-dihydro-4H-1,3-oxazin-4-one, and their herbicidal activities are disclosed in, for example, WO 093/15064.

However, the compounds described in the above-mentioned international publication differ from the compound of this invention since none of them have an acid amide substituent on the 3-position of the 1,3-oxazine ring. Further, the herbicidal activities and selective toxicities of the foregoing known compounds have been unsatisfactory.

SUMMARY OF THE INVENTION

The inventors of the present invention have earnestly studied a variety of 1,3-oxazin-4-one derivatives by synthesizing them and examining their physiological activities. As a result, the inventors found novel 1,3-oxazin-4-one derivatives which have remarkable selective herbicidal activity and exhibit excellent herbicidal activity to various weeds at very small dosages without giving phytotoxicity to useful crops. Thus the present invention has been achieved.

According to the present invention, there are provided 1,3-oxazin-4-one derivatives represented by following general formula (I):

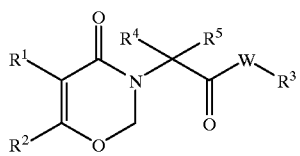

(I)

in which $R^1$ represents a phenyl group which may be substituted; $R^2$ represents a hydrogen atom or a lower alkyl group; $R^3$ represents a hydrogen atom, a lower alkyl group, an aralkyl group or a phenyl group which may be substituted; $R^4$ and $R^5$ each independently represent a lower alkyl group, W represents an oxygen atom or a group represented by the formula —N($R^6$)— in which $R^6$ represents a hydrogen atom, a lower alkyl group, a lower alkenyl group or a lower alkynyl group.

According to the present invention, there also provided herbicidal compositions containing the above derivatives and N-methylene amino acid ester derivatives of intermediates for preparing same, which are represented by following formula (II):

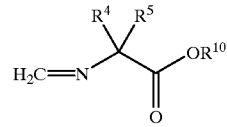

(II)

in which $R^4$ and $R^5$ each independently represent a lower alkyl group; $R^{10}$ represents a lower alkyl group or an aralkyl group.

DESCRIPTION OF THE PREFERRED EMBODIMENTS

The 1,3-oxazin-4-one derivatives and the intermediates for preparing same according to the present invention represented by the general formulae (I) and (II), respectively, are described in detail below.

Atoms and groups of the compounds represented in the general formulae (I) and (II) represented by $R^1$, $R^2$, $R^3$, $R^4$, $R^5$, $R^6$ and $R^{10}$ as defined above are exemplified as follows:

Phenyl Group Which May Be Substituted

A phenyl group or a phenyl group which is substituted by a halogen atom, a hydroxy group, a lower alkyl group, a lower alkoxy group, a phenoxy group, a lower alkylthio group, a lower alkylsulfonyl group, a lower haloalkyl group, a lower haloalkoxy group, an alkoxycarbonyl group, an alkoxycarbonylalkoxy group, an acyl group, a cyano group or a nitro group. Examples of these groups include a phenyl group, a 2-fluorophenyl group, a 3-chlorophenyl group, a 3,5-dichloro-4-hydroxyphenyl group, a 3-toluyl group, a 2,5-xylyl group, a 3-anisyl group, a 3-phenoxyphenyl group, a 3-methylthiophenyl group, a 2-chloro-5-(methylsulfonyl) phenyl group, a 3-(trifluoromethyl)phenyl group, a 3,5-bis (difluoromethoxy)phenyl group, a 3-methoxycarbonylphenyl group, a 3-(1-methoxycarbonyl) ethoxyphenyl group, a 3-nitrophenyl group, a 3-cyanophenyl group, a 3-acetylphenyl group, a 2-chloro-5-nitrophenyl group, a 3,5-dichlorophenyl group, a 2-fluoro-4-chlorophenyl group, a 2,5-dichlorophenyl group, a 3,5-dichloro-4-methylphenyl group, etc.

Halogen Atom

A fluorine atom, a chlorine atom, a bromine atom, or an iodine atom.

Lower Alkyl Group

A lower alkyl group having one to six carbon atoms may be either straight chained or branched chained, such as a methyl group, an ethyl group, a n-propyl group, an isopropyl group, a n-butyl group, an isobutyl group, a sec-butyl group, a tert-butyl group, a n-pentyl group, a neopentyl group, a tert-pentyl group or a hexyl group, etc.

Lower Alkenyl Group

A lower alkenyl group having two to five carbon atoms such as an allyl group, a 2-methyl-2-propenyl group, a 2-butenyl group, a 3-butenyl group, a 3-methyl-2-butenyl group, etc.

Lower Alkynyl Group

A lower alkynyl group having two to five carbon atoms such as a 2-propynyl group, a 1-methyl-2-propynyl group, a 2-butynyl group, a 3-butynyl group, etc.

Lower Alkoxy Group

A lower alkoxy group whose alkyl moiety has the same meanings as defined above, such as a methoxy group, an ethoxy group, a propoxy group, an isopropoxy group, a butoxy group, a pentoxy group, etc.

Lower Alkylthio Group

A lower alkylthio group whose alkyl moiety has the same meanings as defined above, such as a methylthio group, an ethylthio group, a propylthio group, an isopropylthio group, a butylthio group, a pentylthio group, etc.

Lower Alkylsulfonyl Group

A lower alkylsulfonyl group whose alkyl moiety has the same meanings as defined above, such as a methylsulfonyl group, an ethylsulfonyl group, a propylsulfonyl group, an isopropylsulfonyl group, a butylsulfonyl group, a pentylsulfonyl group, etc.

Lower Haloalkyl Group

A lower haloalkyl group having one to four carbon atoms such as a bromomethyl group, a difluoromethyl group, a dichloromethyl group, a trifluoromethyl group, a 1-chloroethyl group, an 2-iodoethyl group, a 3-chloropropyl group, a 2-methyl-2-chloropropyl group, a 2,2,2-trifluoroethyl group, etc.

Lower Haloalkoxy Group

A lower haloalkoxy group whose haloalkyl moiety has the same meanings as defined above, such as a trifluoromethoxy group, a difluoromethoxy group, a chlorodifluoromethoxy group, a 2-chloroethoxy group, a 1,1,2,2-tetrafluoroethoxy group, a 3-chloropropoxy group, etc.

Alkoxycarbonyl Group

An alkoxycarbonyl group having about two to eight carbon atoms such as a methoxycarbonyl group, an ethoxycarbonyl group, an isopropoxycarbonyl group, etc.

Alkoxycarbonylalkoxy Group

An alkoxycarbonylalkoxy group having about three to ten carbon atoms such as a methoxycarbonylmethoxy group, a 1-(methoxycarbonyl)ethoxy group, a 1-(ethoxycarbonyl)ethoxy group, a 1-methyl-3-(isopropoxycarbonyl)propyl group, etc.

Acyl Group

An acyl group such as an acetyl group, a propionyl group, a butyryl group, an isobutyryl group, etc.

Aralkyl Group

An aralkyl group such as a benzyl group, a 1-phenylethyl group, a 2-phenylethyl group, a 1-methyl-1-phenylethyl group, a 1-methyl-2-phenylethyl group, a 1-ethyl-2-phenylethyl group, a 3-phenylpropyl group, etc.

Groups not specifically mentioned as examples of the above groups can be selected by optional combinations based on the above atoms and groups or according to common sense in this field.

Among the compounds represented by general formula (I) described above, preferred groups of the compound include those compounds of general formula (I) in which $R^1$ is a phenyl group, a 2-fluorophenyl group, a 2-chlorophenyl group or a 2-methylphenyl group;

$R^2$ is a hydrogen atom, a methyl group or an ethyl group;

$R^3$ is a phenyl group; a phenyl group substituted at the 3-position by one substituent selected from the group consisting of a halogen atom, a lower alkyl group, a lower alkoxy group, a phenoxy group, a lower haloalkyl group and a lower haloalkoxy group; or a phenyl group substituted at the 2- and 5-positions or 3- and 5-positions by two substituents selected from the group consisting of a halogen atom, a lower alkyl group, a lower alkoxy group, a phenoxy group, a lower haloalkyl group or a lower haloalkoxy group;

$R^4$ and $R^5$ are each independently a methyl group or a ethyl group;

W is a group represented by the formula —N—($R^6$)—, in which the preferred group of $R^6$ is a hydrogen atom or a methyl group.

A more preferred compound of general formula (I) is a compound represented by following general formula (I-1):

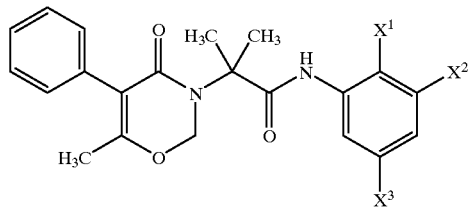

(I-1)

in which $X^1$, $X^2$ and $X^3$ each independently represent a hydrogen atom, a halogen atom, a lower alkyl group, a lower alkoxy group, a phenoxy group, a lower haloalkyl group or a lower haloalkoxy group.

Specific examples of the compound of general formula (I) above provided by the present invention will be shown in Tables 1 to 5 hereinbelow. In the Tables, abbreviations used have the following meanings.

Me: methyl group; Et: ethyl group;

Pr: n-propyl group; iPr: isopropyl group;

Bu: butyl group; iBu: isobutyl group;

sBu: sec-butyl group; tBu: tert-butyl group;

Hex: hexyl group; Ph: phenyl group;

Bn: benzyl group; 2-F-PH: 2-fluorophenyl; and

-: no substituent.

TABLE 1

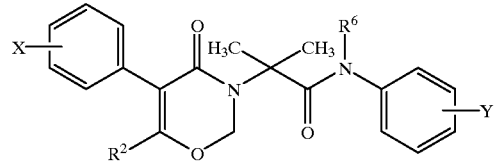

| Compd. No. | X | Y | $R^2$ | $R^6$ | Melting Point [° C.] |
|---|---|---|---|---|---|
| 1 | — | — | Me | H | 134–137 |
| 2 | — | 2-F | Me | H | 129–131 |
| 3 | — | 3-F | Me | H | 131–132.5 |
| 4 | — | 4-F | Me | H | 49–51 |
| 5 | — | 2-Cl | Me | H | 146–148.5 |
| 6 | — | 3-Cl | Me | H | 140.5–144 |
| 7 | — | 4-Cl | Me | H | 86–88 |
| 8 | — | 2-Br | Me | H | |
| 9 | — | 3-Br | Me | H | 105.5–153 |
| 10 | — | 4-Br | Me | H | |
| 11 | — | 2-I | Me | H | |
| 12 | — | 3-I | Me | H | 154–156 |
| 13 | — | 4-I | Me | H | |
| 14 | — | 2-F, 3-F | Me | H | 155–161 |
| 15 | — | 2-F, 4-F | Me | H | 164–168.5 |
| 16 | — | 2-F, 5-F | Me | H | 115–120 |
| 17 | — | 2-F, 6-F | Me | H | 176.5–178 |
| 18 | — | 3-F, 4-F | Me | H | 129–130.5 |
| 19 | — | 3-F, 5-F | Me | H | 177.5–178 |
| 20 | — | 3-F, 4-F, 5-F | Me | H | |
| 21 | — | 2-F, 3-F, 4-F, 5-F, 6-F | Me | H | 192–194 |
| 22 | — | 2-Cl, 3-Cl | Me | H | 138–142 |
| 23 | — | 2-Cl, 4-Cl | Me | H | 144–149 |
| 24 | — | 2-Cl, 5-Cl | Me | H | 173–174 |
| 25 | — | 2-Cl, 6-Cl | Me | H | |
| 26 | — | 3-Cl, 4-Cl | Me | H | 78–81 |
| 27 | — | 3-Cl, 5-Cl | Me | H | 182–184.5 |
| 28 | — | 3-Cl, 4-Cl, 5-Cl | Me | H | 198.5–199.5 |

TABLE 1-continued

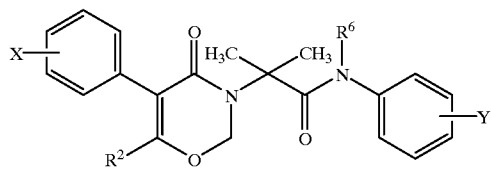

| Compd. No. | X | Y | R² | R⁶ | Melting Point [° C.] |
|---|---|---|---|---|---|
| 29 | — | 2-Cl, 3-Cl, 4-Cl, 5-Cl, 6-Cl | Me | H | |
| 30 | — | 2-F, 4-Cl | Me | H | 126–131 |
| 31 | — | 3-Cl, 4-F | Me | H | 168–169.5 |
| 32 | — | 3-Br, 5-Br | Me | H | |
| 33 | — | 3-Cl, 5-F | Me | H | |
| 34 | — | 2-Me | Me | H | 169–171 |
| 35 | — | 3-Me | Me | H | 155–157 |
| 36 | — | 4-Me | Me | H | 169–171 |
| 37 | — | 2-Me, 3-Me | Me | H | |
| 38 | — | 2-Me, 4-Me | Me | H | |
| 39 | — | 2-Me, 5-Me | Me | H | 132–134 |
| 40 | — | 2-Me, 6-Me | Me | H | 194–197 |
| 41 | — | 3-Me, 4-Me | Me | H | |
| 42 | — | 3-Me, 5-Me | Me | H | 162–166 |
| 43 | — | 3-Me, 4-Me, 5-Me | Me | H | |
| 44 | — | 2-Me, 4-Me, 6-Me | Me | H | |
| 45 | — | 3-Me, 4-Cl | Me | H | |
| 46 | — | 2-Cl, 3-Me, 4-Cl | Me | H | 149–154 |
| 47 | — | 3-Cl, 4-Me, 5-Cl | Me | H | |
| 48 | — | 2-Et | Me | H | |
| 49 | — | 3-Et | Me | H | 118.5–120.5 |
| 50 | — | 4-Et | Me | H | |
| 51 | — | 2-Pr | Me | H | |
| 52 | — | 3-Pr | Me | H | |
| 53 | — | 4-Pr | Me | H | |
| 54 | — | 3-iPr | Me | H | 149–150 |
| 55 | — | 4-iPr | Me | H | |
| 56 | — | 3-Bu | Me | H | |
| 57 | — | 4-Bu | Me | H | |
| 58 | — | 3-iBu | Me | H | |
| 59 | — | 3-sBu | Me | H | |
| 60 | — | 4-tBu | Me | H | |
| 61 | — | 3-Hex | Me | H | |
| 62 | — | 4-Hex | Me | H | |
| 63 | — | 2-OMe | Me | H | 162–164 |
| 64 | — | 3-OMe | Me | H | 138.5–141 |
| 65 | — | 4-OMe | Me | H | 154–155 |
| 66 | — | 2-OMe, 4-OMe | Me | H | |
| 67 | — | 2-OMe, 5-OMe | Me | H | |
| 68 | — | 3-OMe, 5-OMe | Me | H | |
| 69 | — | 3-OMe, 4-OMe, 5-OMe | Me | H | |
| 70 | — | 3-Cl, 4-OMe, 5-Cl | Me | H | |
| 71 | — | 3-Br, 4-OMe, 5-Br | Me | H | |
| 72 | — | 3-Cl, 4-OH, 5-Cl | Me | H | 170–172 |
| 73 | — | 3-Br, 4-OH, 5-Br | Me | H | 154–160.5 |
| 74 | — | 2-OEt | Me | H | |
| 75 | — | 3-OEt | Me | H | |
| 76 | — | 4-OEt | Me | H | |
| 77 | — | 3-OPr | Me | H | |
| 78 | — | 4-OPr | Me | H | |
| 79 | — | 3-OiPr | Me | H | |
| 80 | — | 4-OiPr | Me | H | |
| 81 | — | 3-OBu | Me | H | |
| 82 | — | 2-OiBu | Me | H | |
| 83 | — | 3-OsBu | Me | H | |
| 84 | — | 4-OtBu | Me | H | |
| 85 | — | 3-OHex | Me | H | |
| 86 | — | 4-OHex | Me | H | |
| 87 | — | 2-OPh | Me | H | |
| 88 | — | 3-OPh | Me | H | 140–142.5 |
| 89 | — | 4-OPh | Me | H | |
| 90 | — | 2-OPh, 5-OPh | Me | H | |
| 91 | — | 3-OPh, 5-OPh | Me | H | |
| 92 | — | 2-CF₃ | Me | H | 109.5–111 |

TABLE 1-continued

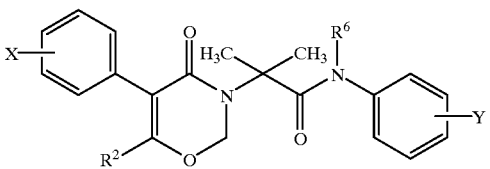

| Compd. No. | X | Y | R² | R⁶ | Melting Point [° C.] |
|---|---|---|---|---|---|
| 93 | — | 3-CF₃ | Me | H | 113.5–114.5 |
| 94 | — | 4-CF₃ | Me | H | 74.5–78 |
| 95 | — | 2-CF₃, 5-CF₃ | Me | H | 177.5–178.5 |
| 96 | — | 3-CF₃, 5-CF₃ | Me | H | 172–175 |
| 97 | — | 2-CH₂CF₃ | Me | H | |
| 98 | — | 3-CH₂CF₃ | Me | H | |
| 99 | — | 4-CH₂CF₃ | Me | H | |
| 100 | — | 2-CH₂CF₃, 5-CH₂CF₃ | Me | H | |
| 101 | — | 3-CH₂CF₃, 5-CH₂CF₃ | Me | H | |
| 102 | — | 2-OCHF₂ | Me | H | 134–140 |
| 103 | — | 3-OCHF₂ | Me | H | 132.5–134 |
| 104 | — | 4-OCHF₂ | Me | H | 127–129 |
| 105 | — | 2-OCHF₂, 5-OCHF₂ | Me | H | |
| 106 | — | 3-OCHF₂, 5-OCHF₂ | Me | H | |
| 107 | — | 3-Cl, 4-OCHF₂, 5-Cl | Me | H | |
| 108 | — | 3-Br, 4-OCHF₂, 5-Br | Me | H | |
| 109 | — | 2-OCF₃ | Me | H | |
| 110 | — | 3-OCF₃ | Me | H | 146–150 |
| 111 | — | 4-OCF₃ | Me | H | |
| 112 | — | 2-OCF₃, 5-OCF₃ | Me | H | |
| 113 | — | 3-OCF₃, 5-OCF₃ | Me | H | |
| 114 | — | 3-Cl, 4-OCF₃, 5-Cl | Me | H | |
| 115 | — | 3-Br, 4-OCF₃, 5-Br | Me | H | |
| 116 | — | 2-OCH₂CF₃ | Me | H | |
| 117 | — | 3-OCH₂CF₃ | Me | H | |
| 118 | — | 4-OCH₂CF₃ | Me | H | |
| 119 | — | 2-OCH₂CF₃, 5-OCH₂CF₃ | Me | H | |
| 120 | — | 3-OCH₂CF₃, 5-OCH₂CF₃ | Me | H | |
| 121 | — | 3-Cl, 4-OCH₂CF₃, 5-Cl | Me | H | |
| 122 | — | 2-CN | Me | H | |
| 123 | — | 3-CN | Me | H | 70–72 |
| 124 | — | 4-CN | Me | H | 84.5–87 |
| 125 | — | 2-CN, 5-CN | Me | H | |
| 126 | — | 3-CN, 5-CN | Me | H | |
| 127 | — | 2-NO₂ | Me | H | 172.5–174.5 |
| 128 | — | 3-NO₂ | Me | H | 165–168 |
| 129 | — | 4-NO₂ | Me | H | 93.5–95 |
| 130 | — | 2-NO₂, 5-NO₂ | Me | H | |
| 131 | — | 3-NO₂, 5-NO₂ | Me | H | 110–115 |
| 132 | — | 2-NO₂, 4-NO₂ | Me | H | |
| 133 | — | 2-CF₃, 4-NO₂ | Me | H | |
| 134 | — | 3-CF₃, 4-NO₂ | Me | H | |
| 135 | — | 2-COOMe | Me | H | 182–184 |
| 136 | — | 3-COOMe | Me | H | 170.5–171 |
| 137 | — | 4-COOMe | Me | H | 132.5–134 |
| 138 | — | 3-COOEt | Me | H | 167.5–171.5 |
| 139 | — | 3-COOtBu | Me | H | |
| 140 | — | 2-OCH₂COOMe | Me | H | |
| 141 | — | 3-OCH₂COOMe | Me | H | 120–123.5 |
| 142 | — | 4-OCH₂COOMe | Me | H | |
| 143 | — | 2-OCH(Me)COOMe | Me | H | |
| 144 | — | 3-OCH(Me)COOMe | Me | H | 131.5–134 |
| 145 | — | 4-OCH(Me)COOMe | Me | H | |
| 146 | — | 2-SMe | Me | H | 146–150 |
| 147 | — | 3-SMe | Me | H | 135–137.5 |
| 148 | — | 4-SMe | Me | H | 169–170 |
| 149 | — | 2-SO₂Me | Me | H | 120–125 |
| 150 | — | 3-SO₂Me | Me | H | |
| 151 | — | 4-SO₂Me | Me | H | Measure- |

TABLE 1-continued

Structure: X-phenyl-substituted oxazine with C(CH₃)₂-C(=O)-N(R⁶)-phenyl-Y group, R² on oxazine ring.

| Compd. No. | X | Y | R² | R⁶ | Melting Point [° C.] |
|---|---|---|---|---|---|
| | | | | | ment Impossible |
| 152 | — | 3-OH | Me | H | 193–196 |
| 153 | — | 4-OH | Me | H | |
| 154 | — | 2-COMe | Me | H | |
| 155 | — | 3-COMe | Me | H | 151.5–154 |
| 156 | — | 4-COMe | Me | H | |
| 157 | — | 3-COEt | Me | H | |
| 158 | — | — | H | H | |
| 159 | — | 3-Cl | H | H | |
| 160 | — | 3-Br | H | H | |
| 161 | — | 3-I | H | H | |
| 162 | — | 3-F, 5-F | H | H | |
| 163 | — | 2-Cl, 5-Cl | H | H | |
| 164 | — | 3-Cl, 5-Cl | H | H | |
| 165 | — | 3-Br, 5-Br | H | H | |
| 166 | — | 3-Me | H | H | |
| 167 | — | 2-Me, 5-Me | H | H | |
| 168 | — | 3-Me, 5-Me | H | H | |
| 169 | — | 3-Et | H | H | |
| 170 | — | 3-Pr | H | H | |
| 171 | — | 3-OMe | H | H | |
| 172 | — | 2-OMe, 5-OMe | H | H | |
| 173 | — | 3-OMe, 5-OMe | H | H | |
| 174 | — | 3-Cl, 4-OMe, 5-Cl | H | H | |
| 175 | — | 3-OPh | H | H | |
| 176 | — | 3-CF₃ | H | H | |
| 177 | — | 2-CF₃, 5-CF₃ | H | H | |
| 178 | — | 3-CF₃, 5-CF₃ | H | H | |
| 179 | — | 3-OCHF₂ | H | H | |
| 180 | — | 2-OCHF₂, 5-OCHF₂ | H | H | |
| 181 | — | 3-OCHF₂, 5-OCHF₂ | H | H | |
| 182 | — | 3-CN | H | H | |
| 183 | — | 3-NO₂ | H | H | |
| 184 | — | 2-NO₂, 5-NO₂ | H | H | |
| 185 | — | 3-NO₂, 5-NO₂ | H | H | |
| 186 | — | — | Et | H | |
| 187 | — | 3-Cl | Et | H | 136–137 |
| 188 | — | 3-Br | Et | H | |
| 189 | — | 3-I | Et | H | |
| 190 | — | 3-F, 5-F | Et | H | |
| 191 | — | 2-Cl, 5-Cl | Et | H | |
| 192 | — | 3-Cl, 5-Cl | Et | H | |
| 193 | — | 3-Br, 5-Br | Et | H | |
| 194 | — | 3-Me | Et | H | |
| 195 | — | 2-Me, 5-Me | Et | H | |
| 196 | — | 3-Me, 5-Me | Et | H | |
| 197 | — | 3-Et | Et | H | |
| 198 | — | 3-Pr | Et | H | |
| 199 | — | 3-OMe | Et | H | |
| 200 | — | 2-OMe, 5-OMe | Et | H | |
| 201 | — | 3-OMe, 5-OMe | Et | H | |
| 202 | — | 3-Cl, 4-OMe, 5-Cl | Et | H | |
| 203 | — | 3-OPh | Et | H | |
| 204 | — | 3-CF₃ | Et | H | 49–51 |
| 205 | — | 2-CF₃, 5-CF₃ | Et | H | |
| 206 | — | 3-CF₃, 5-CF₃ | Et | H | |
| 207 | — | 3-OCHF₂ | Et | H | |
| 208 | — | 2-OCHF₂, 5-OCHF₂ | Et | H | |
| 209 | — | 3-OCHF₂, 5-OCHF₂ | Et | H | |
| 210 | — | — | Pr | H | |
| 211 | — | 3-Cl | Pr | H | 117.5–119 |
| 212 | — | 3-CF₃ | Pr | H | |
| 213 | — | 3-CF₃ | Bu | H | |
| 214 | 2-F | — | Me | H | 139.5–141 |
| 215 | 2-F | 3-Cl | Me | H | 129–134 |
| 216 | 2-F | 3-Br | Me | H | |
| 217 | 2-F | 3-I | Me | H | |
| 218 | 2-F | 3-F, 5-F | Me | H | |
| 219 | 2-F | 2-Cl, 5-Cl | Me | H | |
| 220 | 2-F | 3-Cl, 5-Cl | Me | H | 168–169.5 |
| 221 | 2-F | 3-Br, 5-Br | Me | H | |
| 222 | 2-F | 3-Me | Me | H | |
| 223 | 2-F | 2-Me, 5-Me | Me | H | |
| 224 | 2-F | 3-Me, 5-Me | Me | H | |
| 225 | 2-F | 3-Et | Me | H | |
| 226 | 2-F | 3-Pr | Me | H | |
| 227 | 2-F | 3-OMe | Me | H | |
| 228 | 2-F | 2-OMe, 5-OMe | Me | H | |
| 229 | 2-F | 3-OMe, 5-OMe | Me | H | |
| 230 | 2-F | 3-Cl, 4-OMe, 5-Cl | Me | H | |
| 231 | 2-F | 3-OPh | Me | H | |
| 232 | 2-F | 3-CF₃ | Me | H | |
| 233 | 2-F | 2-CF₃, 5-CF₃ | Me | H | |
| 234 | 2-F | 3-CF₃, 5-CF₃ | Me | H | |
| 235 | 2-F | 3-OCHF₂ | Me | H | |
| 236 | 2-F | 2-OCHF₂, 5-OCHF₂ | Me | H | |
| 237 | 2-F | 3-OCHF₂, 5-OCHF₂ | Me | H | |
| 238 | 2-F | 3-CN | Me | H | |
| 239 | 2-F | 3-NO₂ | Me | H | |
| 240 | 2-F | 2-NO₂, 5-NO₂ | Me | H | |
| 241 | 2-F | 3-NO₂, 5-NO₂ | Me | H | |
| 242 | 2-Cl | — | Me | H | |
| 243 | 2-Cl | 3-Cl | Me | H | |
| 244 | 2-Cl | 3-Br | Me | H | |
| 245 | 2-Cl | 3-I | Me | H | |
| 246 | 2-Cl | 3-F, 5-F | Me | H | |
| 247 | 2-Cl | 2-Cl, 5-Cl | Me | H | |
| 248 | 2-Cl | 3-Cl, 5-Cl | Me | H | |
| 249 | 2-Cl | 3-Br, 5-Br | Me | H | |
| 250 | 2-Cl | 3-Me | Me | H | |
| 251 | 2-Cl | 2-Me, 5-Me | Me | H | |
| 252 | 2-Cl | 3-Me, 5-Me | Me | H | |
| 253 | 2-Cl | 3-Et | Me | H | |
| 254 | 2-Cl | 3-Pr | Me | H | |
| 255 | 2-Cl | 3-OMe | Me | H | |
| 256 | 2-Cl | 2-OMe, 5-OMe | Me | H | |
| 257 | 2-Cl | 3-OMe, 5-OMe | Me | H | |
| 258 | 2-Cl | 3-Cl, 4-OMe, 5-Cl | Me | H | |
| 259 | 2-Cl | 3-OPh | Me | H | |
| 260 | 2-Cl | 3-CF₃ | Me | H | |
| 261 | 2-Cl | 2-CF₃, 5-CF₃ | Me | H | |
| 262 | 2-Cl | 3-CF₃, 5-CF₃ | Me | H | |
| 263 | 2-Cl | 3-OCHF₂ | Me | H | |
| 264 | 2-Cl | 2-OCHF₂, 5-OCHF₂ | Me | H | |
| 265 | 2-Cl | 3-OCHF₂, 5-OCHF₂ | Me | H | |
| 266 | 2-Cl | 3-CN | Me | H | |
| 267 | 2-Cl | 3-NO₂ | Me | H | |
| 268 | 2-Cl | 2-NO₂, 5-NO₂ | Me | H | |
| 269 | 2-Cl | 3-NO₂, 5-NO₂ | Me | H | |
| 270 | 2-Me | — | Me | H | |
| 271 | 2-Me | 3-Cl | Me | H | |
| 272 | 2-Me | 3-Br | Me | H | |
| 273 | 2-Me | 3-I | Me | H | |
| 274 | 2-Me | 3-F, 5-F | Me | H | |
| 275 | 2-Me | 2-Cl, 5-Cl | Me | H | |
| 276 | 2-Me | 3-Cl, 5-Cl | Me | H | |
| 277 | 2-Me | 3-Br, 5-Br | Me | H | |
| 278 | 2-Me | 3-Me | Me | H | |
| 279 | 2-Me | 2-Me, 5-Me | Me | H | |
| 280 | 2-Me | 3-Me, 5-Me | Me | H | |
| 281 | 2-Me | 3-Et | Me | H | |

TABLE 1-continued

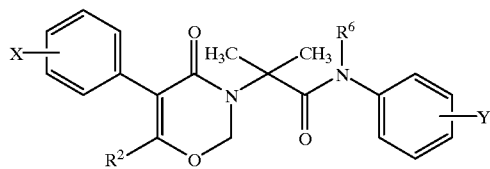

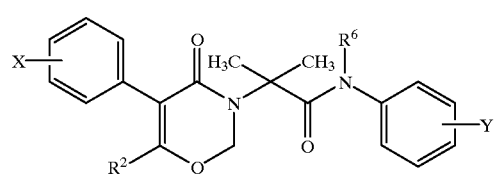

| Compd. No. | X | Y | R² | R⁶ | Melting Point [° C.] |
|---|---|---|---|---|---|
| 282 | 2-Me | 3-Pr | Me | H | |
| 283 | 2-Me | 3-OMe | Me | H | |
| 284 | 2-Me | 2-OMe, 5-OMe | Me | H | |
| 285 | 2-Me | 3-OMe, 5-OMe | Me | H | |
| 286 | 2-Me | 3-Cl, 4-OMe, 5-Cl | Me | H | |
| 287 | 2-Me | 3-OPh | Me | H | |
| 288 | 2-Me | 3-CF₃ | Me | H | |
| 289 | 2-Me | 2-CF₃, 5-CF₃ | Me | H | |
| 290 | 2-Me | 3-CF₃, 5-CF₃ | Me | H | |
| 291 | 2-Me | 3-OCHF₂ | Me | H | |
| 292 | 2-Me | 2-OCHF₂, 5-OCHF₂ | Me | H | |
| 293 | 2-Me | 3-OCHF₂, 5-OCHF₂ | Me | H | |
| 294 | 2-Me | 3-CN | Me | H | |
| 295 | 2-Me | 3-NO₂ | Me | H | |
| 296 | 2-Me | 2-NO₂, 5-NO₂ | Me | H | |
| 297 | 2-Me | 3-NO₂, 5-NO₂ | Me | H | |
| 298 | — | — | Me | Me | 186–187 |
| 299 | — | 3-Cl | Me | Me | |
| 300 | — | 3-Br | Me | Me | |
| 301 | — | 2-Cl, 5-Cl | Me | Me | |
| 302 | — | 3-Cl, 5-Cl | Me | Me | 64–67 |
| 303 | — | 3-Me | Me | Me | |
| 304 | — | 2-Me, 5-Me | Me | Me | |
| 305 | — | 3-Me, 5-Me | Me | Me | |
| 306 | — | 3-Et | Me | Me | |
| 307 | — | 3-Pr | Me | Me | |
| 308 | — | 3-OMe | Me | Me | |
| 309 | — | 2-OMe, 5-OMe | Me | Me | |
| 310 | — | 3-OMe, 5-OMe | Me | Me | |
| 311 | — | 3-OPh | Me | Me | |
| 312 | — | 3-CF₃ | Me | Me | |
| 313 | — | 3-OCHF₂ | Me | Me | |
| 314 | — | 3-NO₂ | Me | Me | |
| 315 | — | 2-NO₂, 5-NO₂ | Me | Me | |
| 316 | — | 3-NO₂, 5-NO₂ | Me | Me | |
| 317 | — | — | Me | Et | |
| 318 | — | 3-Cl | Me | Et | |
| 319 | — | 2-Cl, 5-Cl | Me | Et | |
| 320 | — | 3-Cl, 5-Cl | Me | Et | |
| 321 | — | 3-Me | Me | Et | |
| 322 | — | 2-Me, 5-Me | Me | Et | |
| 323 | — | 3-Me, 5-Me | Me | Et | |
| 324 | — | 3-Et | Me | Et | |
| 325 | — | — | Me | CH₂CH=CH₂ | |
| 326 | — | 3-Cl | Me | CH₂CH=CH₂ | |
| 327 | — | 2-Cl, 5-Cl | Me | CH₂CH=CH₂ | |
| 328 | — | 3-Cl, 5-Cl | Me | CH₂CH=CH₂ | |
| 329 | — | 3-Me | Me | CH₂CH=CH₂ | |
| 330 | — | 3-CF₃ | Me | CH₂CH=CH₂ | |
| 331 | — | 3-OCHF₂ | Me | CH₂CH=CH₂ | |
| 332 | — | — | Me | CH₂C≡CH | |
| 333 | — | 3-Cl | Me | CH₂C≡CH | |
| 334 | — | 2-Cl, 5-Cl | Me | CH₂C≡CH | |
| 335 | — | 3-Cl, 5-Cl | Me | CH₂C≡CH | |
| 336 | — | 3-Me | Me | CH₂C≡CH | |
| 337 | — | 3-CF₃ | Me | CH₂C≡CH | |
| 338 | — | 3-OCHF₂ | Me | CH₂C≡CH | |
| 339 | — | 2-F, 3-F, 4-F | Me | H | 169.5–172.5 |
| 340 | — | 2-F, 3-F, 5-F | Me | H | |
| 341 | — | 2-F, 3-F, 6-F | Me | H | 148.5–151 |
| 342 | — | 2-F, 4-F, 5-F | Me | H | 137.5–139.5 |
| 343 | — | 2-F, 4-F, 6-F | Me | H | 177–179 |
| 344 | — | 2-F, 3-F, 4-F, 5-F | Me | H | 121.5–124.5 |
| 345 | — | 2-F, 3-F, 4-F, 6-F | Me | H | 146–148 |
| 346 | — | 2-F, 3-F, 5-F, 6-F | Me | H | 135.5–137 |
| 347 | — | 2-Cl, 3-Cl, 5-Cl | Me | H | |
| 348 | — | 2-Cl, 4-Cl, 5-Cl | Me | H | |
| 349 | — | 2-Cl, 3-Cl, 4-Cl, 5-Cl | Me | H | 176–177 |
| 350 | — | 2-F, 5-Cl | Me | H | 141–144.5 |
| 351 | — | 2-F, 5-Br | Me | H | |
| 352 | — | 2-F, 5-I | Me | H | |
| 353 | — | 2-F, 4-Br | Me | H | 127–134 |
| 354 | — | 2-F, 3-F, 4-Br, 5-F, 6-F | Me | H | 186–187 |
| 355 | — | 2-F, 3-Cl, 5-Cl | Me | H | |
| 356 | — | 3-tBu, 5-tBu | Me | H | 186.5–187.5 |
| 357 | — | 2-F, 5-Me | Me | H | |
| 358 | — | 2-F, 5-Et | Me | H | |
| 359 | — | 2-F, 5-iPr | Me | H | |
| 360 | — | 2-F, 5-tBu | Me | H | |
| 361 | — | 3-Br, 4-Me, 5-Br | Me | H | 176.5–178.5 |
| 362 | — | 2-F, 3-CF₃ | Me | H | 126.5–128.5 |
| 363 | — | 2-F, 5-CF₃ | Me | H | 146.5–149 |
| 364 | — | 3-CF₃, 4-F | Me | H | 152–154 |
| 365 | — | 3-CF₃, 4-Cl | Me | H | 153–155.5 |
| 366 | — | 2-F, 5-OH | Me | H | |
| 367 | — | 2-F, 5-OMe | Me | H | |
| 368 | — | 2-F, 5-OPh | Me | H | |
| 369 | — | 3-F, 5-OPh | Me | H | 58–61 |
| 370 | — | 3-Cl, 4-OH | Me | H | 92–93.5 |
| 371 | — | 2-F, 4-Cl, 5-OiPr | Me | H | 180–182.5 |
| 372 | — | 2-F, 5-OCHF₂ | Me | H | |
| 373 | — | 3-F, 5-OCHF₂ | Me | H | |
| 374 | — | 2-F, 5-NO₂ | Me | H | 148–150.5 |
| 375 | — | 3-F, 5-NO₂ | Me | H | |
| 376 | — | 3-NO₂, 4-F | Me | H | 161.5–164 |
| 377 | — | 3-F, 5-CF₃ | Me | H | |
| 378 | — | 3-Cl, 5-CF₃ | Me | H | |
| 379 | — | 3-F, 5-Me | Me | H | |
| 380 | — | 3-F, 5-OCHF₂ | Me | H | |
| 381 | 2-F | 2-F, 5-Cl | Me | H | |
| 382 | 2-F | 2-F, 5-Br | Me | H | |
| 383 | 2-F | 2-F, 5-I | Me | H | |
| 384 | 2-F | 2-F, 5-Cl | Me | H | |
| 385 | 2-F | 2-F, 3-Cl, 5-Cl | Me | H | |
| 386 | 2-F | 2-F, 5-Me | Me | H | |
| 387 | 2-F | 2-F, 5-Et | Me | H | |
| 388 | 2-F | 2-F, 5-iPr | Me | H | |
| 389 | 2-F | 2-F, 5-tBu | Me | H | |
| 390 | 2-F | 2-F, 3-CF₃ | Me | H | |
| 391 | 2-F | 2-F, 5-CF₃ | Me | H | |
| 392 | 2-F | 3-F, 5-CF₃ | Me | H | |
| 393 | 2-F | 3-CF₃, 4-Cl | Me | H | |
| 394 | 2-F | 2-F, 5-OH | Me | H | |
| 395 | 2-F | 2-F, 5-OMe | Me | H | |
| 396 | 2-F | 2-F, 5-OPh | Me | H | |
| 397 | 2-F | 3-F, 5-OPh | Me | H | |
| 398 | 2-F | 2-F, 5-OCHF₂ | Me | H | |
| 399 | 2-F | 3-F, 5-OCHF₂ | Me | H | |

TABLE 2

Structure: Ph, H3C on oxazine ring with R4, R5, C(=O)NH-phenyl-Y

| Compd. No. | R⁴ | R⁵ | Y | Melting Point [° C.] |
|---|---|---|---|---|
| 400 | Me | Et | — | |
| 401 | Me | Et | 3-Cl | |
| 402 | Me | Et | 3-Br | |
| 403 | Me | Et | 3-I | |
| 404 | Me | Et | 3-F, 5-F | |
| 405 | Me | Et | 2-Cl, 5-Cl | |
| 406 | Me | Et | 3-Cl, 5-Cl | |
| 407 | Me | Et | 3-Br, 5-Br | |
| 408 | Me | Et | 3-Me | |
| 409 | Me | Et | 2-Me, 5-Me | |
| 410 | Me | Et | 3-Me, 5-Me | |
| 411 | Me | Et | 3-Et | |
| 412 | Me | Et | 3-Pr | |
| 413 | Me | Et | 3-OMe | |
| 414 | Me | Et | 2-OMe, 5-OMe | |
| 415 | Me | Et | 3-OMe, 5-OMe | |
| 416 | Me | Et | 3-Cl, 4-OMe, 5-Cl | |
| 417 | Me | Et | 3-OPh | |
| 418 | Me | Et | 3-CF₃ | |
| 419 | Me | Et | 2-CF₃, 5-CF₃ | |
| 420 | Me | Et | 3-CF₃, 5-CF₃ | |
| 421 | Me | Et | 3-OCHF₂ | |
| 422 | Me | Et | 2-OCHF₂, 5-OCHF₂ | |
| 423 | Me | Et | 3-OCHF₂, 5-OCHF₂ | |
| 424 | Me | Et | 3-CN | |
| 425 | Me | Et | 3-NO₂ | |
| 426 | Me | Et | 2-NO₂, 5-NO₂ | |
| 427 | Me | Et | 3-NO₂, 5-NO₂ | |
| 428 | Me | iPr | — | |
| 429 | Me | iPr | 3-Cl | |
| 430 | Me | iPr | 2-Cl, 5-Cl | |
| 431 | Me | iPr | 3-Cl, 5-Cl | |
| 432 | Me | iPr | 3-Me | |
| 433 | Me | iPr | 2-Me, 5-Me | |
| 434 | Me | iPr | 3-Me, 5-Me | |
| 435 | Me | iBu | — | |
| 436 | Me | iBu | 3-Cl | |
| 437 | Me | iBu | 2-Cl, 5-Cl | |
| 438 | Me | iBu | 3-Cl, 5-Cl | |
| 439 | Me | iBu | 3-Me | |
| 440 | Me | iBu | 2-Me, 5-Me | |
| 441 | Me | iBu | 3-Me, 5-Me | |
| 442 | Et | Et | — | |
| 443 | Et | Et | 3-Cl | |
| 444 | Et | Et | 2-Cl, 5-Cl | |
| 445 | Et | Et | 3-Cl, 5-Cl | |
| 446 | Et | Et | 3-Me | |
| 447 | Et | Et | 2-Me, 5-Me | |
| 448 | Et | Et | 3-Me, 5-Me | |

TABLE 3

Structure: Ph, H3C on oxazine ring with R4, R5, C(=O)O-phenyl-Y

| Compd. No. | R⁴ | R⁵ | Y | Melting Point [° C.] |
|---|---|---|---|---|
| 500 | Me | Me | — | |
| 501 | Me | Me | 3-Cl | |
| 502 | Me | Me | 3-Br | |
| 503 | Me | Me | 3-I | |
| 504 | Me | Me | 3-F, 5-F | |
| 505 | Me | Me | 2-Cl, 5-Cl | |
| 506 | Me | Me | 3-Cl, 5-Cl | Oily |
| 507 | Me | Me | 3-Br, 5-Br | |
| 508 | Me | Me | 3-Me | |
| 509 | Me | Me | 2-Me, 5-Me | |
| 510 | Me | Me | 3-Me, 5-Me | |
| 511 | Me | Me | 3-Et | |
| 512 | Me | Me | 3-Pr | |
| 513 | Me | Me | 3-OMe | |
| 514 | Me | Me | 2-OMe, 5-OMe | |
| 515 | Me | Me | 3-OMe, 5-OMe | |
| 516 | Me | Me | 3-Cl, 4-OMe, 5-Cl | |
| 517 | Me | Me | 3-OPh | |
| 518 | Me | Me | 3-CF₃ | |
| 519 | Me | Me | 2-CF₃, 5-CF₃ | |
| 520 | Me | Me | 3-CF₃, 5-CF₃ | |
| 521 | Me | Me | 3-OCHF₂ | |
| 522 | Me | Me | 2-OCHF₂, 5-OCHF₂ | |
| 523 | Me | Me | 3-OCHF₂, 5-OCHF₂ | |
| 524 | Me | Me | 3-CN | |
| 525 | Me | Me | 3-NO₂ | |
| 526 | Me | Me | 2-NO₂, 5-NO₂ | |
| 527 | Me | Me | 3-NO₂, 5-NO₂ | |
| 528 | Me | Et | — | |
| 529 | Me | Et | 3-Cl | |
| 530 | Me | Et | 2-Cl, 5-Cl | |
| 531 | Me | Et | 3-Cl, 5-Cl | |
| 532 | Me | Et | 3-Me | |
| 533 | Me | Et | 2-Me, 5-Me | |
| 534 | Me | Et | 3-Me, 5-Me | |
| 535 | Me | Et | 3-Et | |
| 536 | Me | Et | 3-OMe | |
| 537 | Me | Et | 3-OPh | |
| 538 | Me | Et | 3-CF₃ | |
| 539 | Me | Et | 3-OCHF₃ | |
| 540 | Me | Et | 3-NO₂ | |
| 541 | Me | iPr | — | |
| 542 | Me | iPr | 3-Cl | |
| 543 | Me | iPr | 2-Cl, 5-Cl | |
| 544 | Me | iPr | 3-Cl, 5-Cl | |
| 545 | Me | iPr | 3-Me | |
| 546 | Me | iPr | 2-Me, 5-Me | |
| 547 | Me | iPr | 3-Me, 5-Me | |
| 548 | Me | iBu | — | |
| 549 | Me | iBu | 3-Cl | |
| 550 | Me | iBu | 2-Cl, 5-Cl | |
| 551 | Me | iBu | 3-Cl, 5-Cl | |
| 552 | Me | iBu | 3-Me | |
| 553 | Me | iBu | 2-Me, 5-Me | |
| 554 | Me | iBu | 3-Me, 5-Me | |
| 555 | Et | Et | — | |
| 556 | Et | Et | 3-Cl | |
| 557 | Et | Et | 2-Cl, 5-Cl | |
| 558 | Et | Et | 3-Cl, 5-Cl | |
| 559 | Et | Et | 3-Me | |
| 560 | Et | Et | 2-Me, 5-Me | |
| 561 | Et | Et | 3-Me, 5-Me | |

TABLE 4

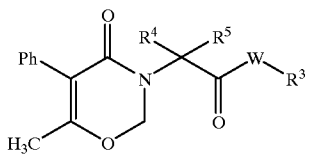

| Compd. No. | R⁴ | R⁵ | W | R³ | Melting Point [° C.] |
|---|---|---|---|---|---|
| 600 | Me | Me | NH | H | 185.5–189 |
| 601 | Me | Me | NH | Me | |
| 602 | Me | Me | NH | Et | |
| 603 | Me | Me | NH | Pr | |
| 604 | Me | Me | NH | iPr | 129–131.5 |
| 605 | Me | Me | NH | Bu | |
| 606 | Me | Me | NH | iBu | 118.5–121 |
| 607 | Me | Me | NH | sBu | |
| 608 | Me | Me | NH | tBu | 145.5–147 |
| 609 | Me | Me | NH | Hex | |
| 610 | Me | Me | NH | Bn | |
| 611 | Me | Me | NH | CH(Me)Ph | |
| 612 | Me | Me | NH | C(Me)₂Ph | 200–201.5 |
| 613 | Me | Me | NH | CH₂CH₂Ph | 130–132 |
| 614 | Me | Me | NH | CH₂CH₂CH₂Ph | |
| 615 | Me | Et | NH | H | |
| 616 | Me | Et | NH | Me | |
| 617 | Me | Et | NH | Et | |
| 618 | Me | Et | NH | Bn | |
| 619 | Me | Et | NH | CH(Me)Ph | |
| 620 | Me | Et | NH | C(Me)₂Ph | |
| 621 | Me | Et | NH | CH₂CH₂Ph | |
| 622 | Me | iBu | NH | Bn | |
| 623 | Me | Me | NMe | H | |
| 624 | Me | Me | NMe | Me | 112–117 |
| 625 | Me | Me | NMe | Et | |
| 626 | Me | Me | NMe | Pr | |
| 627 | Me | Me | NMe | iPr | |
| 628 | Me | Me | NMe | Bu | |
| 629 | Me | Me | NMe | Bn | |
| 630 | Me | Me | NMe | CH(Me)Ph | |
| 631 | Me | Me | NMe | C(Me)₂Ph | |
| 632 | Me | Me | NMe | CH₂CH₂Ph | |
| 633 | Me | Me | NMe | CH₂CH₂CH₂Ph | |
| 634 | Me | Me | O | H | 202–205 |
| 635 | Me | Me | O | Me | 67–69 |
| 636 | Me | Me | O | Et | Oily |
| 637 | Me | Me | O | Pr | |
| 638 | Me | Me | O | iPr | Oily |
| 639 | Me | Me | O | Bu | |
| 641 | Me | Me | O | iBu | |
| 642 | Me | Me | O | sBu | |
| 643 | Me | Me | O | tBu | |
| 644 | Me | Me | O | Hex | |
| 645 | Me | Me | O | Bn | Oily |
| 646 | Me | Me | O | CH(Me)Ph | |
| 647 | Me | Me | O | C(Me)₂Ph | |
| 648 | Me | Me | O | CH₂CH₂Ph | |
| 649 | Me | Me | O | CH₂CH₂CH₂Ph | |
| 650 | Me | Et | O | H | 184–187 |
| 651 | Me | Et | O | Me | Oily |
| 652 | Me | Et | O | Et | |
| 653 | Me | Et | O | Pr | |
| 654 | Me | Et | O | iPr | |
| 655 | Me | Et | O | Bu | |
| 656 | Me | Et | O | iBu | |
| 657 | Me | Et | O | Bn | |
| 658 | Me | Et | O | CH(Me)Ph | |
| 659 | Me | Et | O | C(Me)₂Ph | |
| 660 | Me | Et | O | CH₂CH₂Ph | |
| 661 | Me | iPr | O | H | |
| 662 | Me | iPr | O | Me | |
| 663 | Me | iPr | O | Et | |
| 664 | Me | iPr | O | Pr | |
| 665 | Me | iPr | O | iPr | |
| 666 | Me | iPr | O | Bu | |
| 667 | Me | iPr | O | iBu | |

TABLE 4-continued

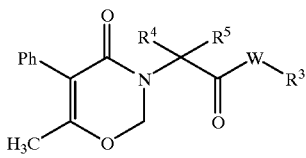

| Compd. No. | R⁴ | R⁵ | W | R³ | Melting Point [° C.] |
|---|---|---|---|---|---|
| 668 | Me | iPr | O | Bn | |
| 669 | Me | iPr | O | CH(Me)Ph | |
| 670 | Me | iPr | O | C(Me)₂Ph | |
| 671 | Me | iBu | O | H | |
| 672 | Me | iBu | O | Me | |
| 673 | Me | iBu | O | Et | |
| 674 | Me | iBu | O | iPr | |
| 675 | Me | iBu | O | iBu | |
| 676 | Me | iBu | O | Bn | |

TABLE 5

| Compd. No. | R¹ | R² | W | R³ | Melting Point [° C.] |
|---|---|---|---|---|---|
| 680 | 2-F—Ph | Me | O | H | 182–183.5 |
| 681 | 2-F—Ph | Me | O | Me | |
| 682 | 2-F—Ph | Me | O | Et | |
| 683 | 2-F—Ph | Me | O | Bn | Oily |
| 684 | Ph | Et | O | H | 152.5–153.5 |
| 685 | Ph | Et | O | Me | |
| 686 | Ph | Et | O | Et | |
| 687 | Ph | Et | O | Bn | 99–100 |
| 688 | Ph | Pr | O | H | 120–122 |
| 689 | Ph | Pr | O | Et | |
| 690 | Ph | Pr | O | Bn | 53–56 |

The compound according to the present invention may be manufactured using any methods known in the art. For example, the compound represented by general formula (I) may be manufactured using the following methods.

Method A

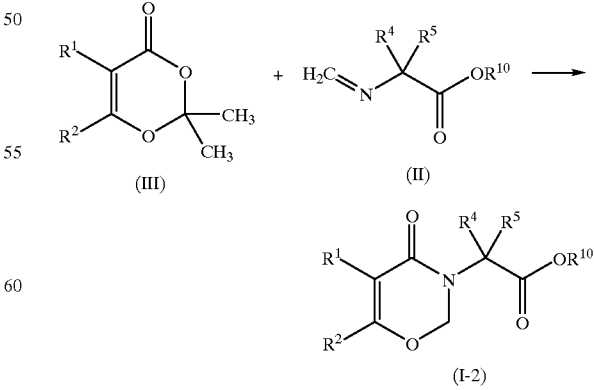

in which $R^1$, $R^2$, $R^4$ and $R^5$ are as defined in general formula (I) and $R^{10}$ is as defined in general formula (II).

The compound of formula (I-2) can be obtained by reacting a compound of formula (II) with a compound of formula (III) in the presence or absence of an adequate solvent.

The reaction temperature can be arbitrarily determined so far as it ranges from 90° C. to 160° C. or to the boiling point of the solvent.

The solvent, if used, is not particularly limited so far as it is inert with starting materials under the conditions of Method A, but in view of the reaction temperature, it is preferably a solvent having a higher boiling point, such as toluene, xylene or mesitylene.

Although the reaction time varies depending upon the setting conditions, the reaction can usually be completed in 1 to 240 minutes.

Although the quantitative ratio of the compounds of formulae (II) and (III) is not particularly limited, the compound of formula (III) is usually 0.5 to 2 moles, preferably 0.9 to 1.1 moles, per 1 mole of the compound of formula (II).

The products of formula (I-2) can be isolated and purified from the reaction mixture using a known method, such as extraction, recrystallization or chromatography.

The N-methylene amino acid ester derivative represented by general formula (II) shown below and used in the above reaction as a starting material is a novel compound, which is also included in the scope of the present invention.

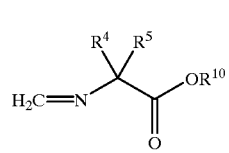

(II)

in which $R^4$ and $R^5$ each independently represent a lower alkyl group, and $R^{10}$ represents a lower alkyl group or an aralkyl group.

Among the compounds represented by general formula (II) described above, preferred groups of the compound include those compounds of general formula (II) in which $R^4$ and $R^5$ are each independently a methyl group or an ethyl group; and $R^{10}$ is a methyl group, an ethyl group or a benzyl group.

Specific examples of the compound of general formula (II) above provided by the present invention are shown in Table 6 hereinbelow. In Table 6, the abbreviations used are the same as in the foregoing Tables.

TABLE 6

| Compd. No. | $R^4$ | $R^5$ | $R^{10}$ |
|---|---|---|---|
| 2-1 | Me | Me | Me |
| 2-2 | Me | Me | Et |
| 2-3 | Me | Me | Pr |
| 2-4 | Me | Me | iPr |
| 2-5 | Me | Me | Bu |
| 2-6 | Me | Me | iBu |
| 2-7 | Me | Me | sBu |
| 2-8 | Me | Me | tBu |
| 2-9 | Me | Me | Hex |
| 2-10 | Me | Me | Bn |
| 2-11 | Me | Me | CH(Me)Ph |

TABLE 6-continued

| Compd. No. | $R^4$ | $R^5$ | $R^{10}$ |
|---|---|---|---|
| 2-12 | Me | Me | C(Me)$_2$Ph |
| 2-13 | Me | Me | CH$_2$CH$_2$Ph |
| 2-14 | Me | Me | CH$_2$CH$_2$CH$_2$Ph |
| 2-15 | Me | Et | Me |
| 2-16 | Me | Et | Et |
| 2-17 | Me | Et | Pr |
| 2-18 | Me | Et | iPr |
| 2-19 | Me | Et | Bu |
| 2-20 | Me | Et | iBu |
| 2-21 | Me | Et | sBu |
| 2-22 | Me | Et | tBu |
| 2-23 | Me | Et | Hex |
| 2-24 | Me | Et | Bn |
| 2-25 | Me | Et | CH(Me)Ph |
| 2-26 | Me | Et | C(Me)$_2$Ph |
| 2-27 | Me | Et | CH$_2$CH$_2$Ph |
| 2-28 | Me | Et | CH$_2$CH$_2$CH$_2$Ph |
| 2-29 | Me | iPr | Me |
| 2-30 | Me | iPr | Et |
| 2-31 | Me | iPr | iPr |
| 2-32 | Me | iPr | Bu |
| 2-33 | Me | iPr | tBu |
| 2-34 | Me | iPr | Bn |
| 2-35 | Me | iPr | CH(Me)Ph |
| 2-36 | Me | iPr | C(Me)$_2$Ph |
| 2-37 | Me | iPr | CH$_2$CH$_2$Ph |
| 2-38 | Me | iBu | Me |
| 2-39 | Me | iBu | Et |
| 2-40 | Me | iBu | iPr |
| 2-41 | Me | iBu | Bu |
| 2-42 | Me | iBu | tBu |
| 2-43 | Me | iBu | Bn |
| 2-44 | Me | iBu | CH(Me)Ph |
| 2-45 | Me | iBu | C(Me)$_3$Ph |
| 2-46 | Me | iBu | CH$_2$CH$_2$Ph |
| 2-47 | Et | Et | Me |
| 2-48 | Et | Et | Et |
| 2-49 | Et | Et | Bn |

The compound of formula (II) may be manufactured using any method known in the art. For example, it may be manufactured using the following method.

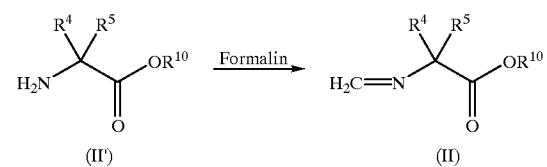

(II')        (II)

in which $R^4$ and $R^5$ are as defined in general formula (I) and $R^{10}$ is as defined in general formula (II).

The compound of formula (II) can be obtained by reacting one of amino acid esters of formula (II') with formalin in the presence or absence of an adequate solvent.

The reaction temperature can be arbitrarily determined so far as it ranges from about 0° C. to 140° C.

The solvent, if used, is not particularly limited so far as it is inert with the materials under the conditions of this method, and preferred examples of the solvent include hydrocarbons such as toluene or xylene; ethers such as diethyl ether, diisopropyl ether or tetrahydrofuran.

Although the reaction time varies depending upon the conditions, the reaction can usually be completed in 1 hour to 1 day.

Although the quantitative ratio of the compounds of formula (II') and formalin is not particularly limited, formalin is usually 1 to 5 moles, preferably 1.1 to 2 moles, per 1 mole of the compound of formula (II').

The products of formula (II) can be isolated and purified from the reaction mixture using a known method, such as extraction, distillation, recrystallization or chromatography.

The amino acid esters of formula (II') used in the above reaction as a starting material can be obtained by known methods or methods similar thereto.

The compound of formula (II) often makes an equilibrium condition with trimers thereof around room temperature, and thus said compound may be present as a mixture of the compound itself, that is monomers and trimers thereof. In addition, the whole compound may be present in the form of a trimer depending upon the condition. However, the monomer name of said compound will be used no matter what form it takes so as to avoid unnessecary complication.

The compound of formula (III) is another starting material for synthesizing the compound of formula (I-2) and can be obtained by several methods, for example by the method described in Chem. Pharm. Bull., 1(6), 1896–1901 (1983) or methods similar thereto.

Method B

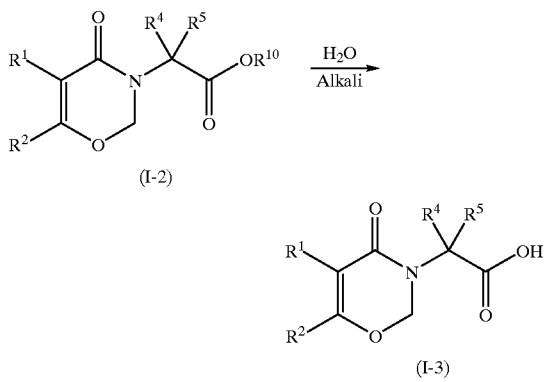

in which $R^1$, $R^2$, $R^4$ and $R^5$ are as defined in general formula (I) and $R^{10}$ is as defined in general formula (II).

The compound of formula (I-3) can be obtained by hydrolyzing the compound of formula (I-2) with an alkali.

Examples of an alkali include a solution of sodium hydroxide or potassium hydroxide.

The solvent, if used in addition to water, is not particularly limited so far as it is inert under the conditions of Method B, and preferred examples of the solvent include alcohols such as methanol or ethanol; ethers such as tetrahydrofuran or dioxane.

The reaction temperature is preferably about from room temperature to 80° C.

The products of formula (I-3) can be isolated and purified from the reaction mixture using a known method, such as extraction, recrystallization or chromatography.

Method C

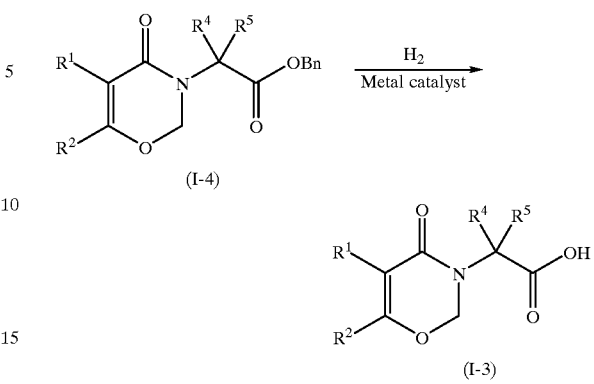

in which $R^1$, $R^2$, $R^4$ and $R^5$ are as defined in general formula (I) and the abbreviation of Bn means a benzyl group.

The compound of formula (I-3) can be obtained by hydrogenating the compound of formula (I-4) in the presence of a metal catalyst.

Most of the metal catalysts commonly used as a catalyst for promoting hydrogenation, such as palladium-carbon, rhodium-carbon or platinum black, can be used as a metal catalyst for this method.

The solvent used is not particularly limited so far as it is inert under the condition of Method C, and preferred examples of the solvent include alcohols such as methanol or ethanol; acetic acid esters such as ethyl acetate; and acetic acid.

This reaction may be completed under the following conditions; hydrogen atmosphere; normal pressure; room temperature; reaction time of from 1 hour to 1 day, and it also may be promoted by applying heat and/or pressure.

The amount of the catalyst added can be arbitrarily determined according to the reaction rate.

The products of formula (I-3) can be isolated and purified from the reaction mixture using a known method, such as extraction, recrystallization or chromatography.

Method D

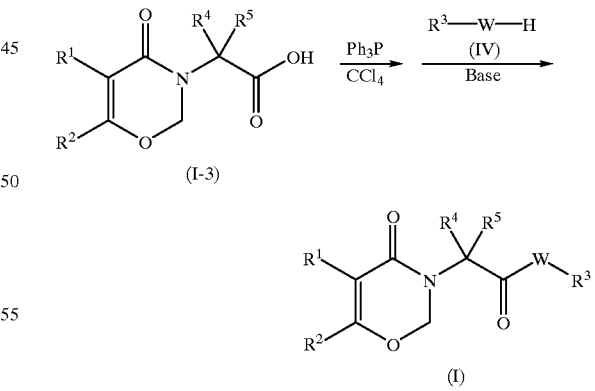

in which $R^1$, $R^2$, $R^3$, $R^4$, $R^5$ and W are as defined in general formula (I).

The compound of formula (I) can be obtained by reacting the compound of formula (I-3) with carbon tetrachloride and triphenylphosphine followed by treatment with the compound of formula (IV) in the presence of base.

The reaction temperature is preferably from room temperature to about 140° C. or to the boiling point of the solvent for the first process above, and 0° C. to about 60° C. for the second process.

The solvent used is not particularly limited so far as it is inert under the conditions of Method D, and preferred examples of the solvent include halogenated hydrocarbon solvents such as carbon tetrachloride, chloroform or methylene chloride; hydrocarbon solvents such as toluene, xylene or mesitylene; and ether solvents such as diethyl ether, tetrahydrofuran or dimethoxyethane.

Examples of a base include tertiary amines such as triethylamine, diisopropylethylamine or pyridine; inorganic bases such as sodium hydroxide or sodium carbonate. If required, the base can also be applied as a water solution or as a salt formed with the compound of formula (IV). Furthermore, when the compound (IV) is an amine, an excess of said compound of formula (IV) can also be used as a base.

The products of formula (I) can be isolated and purified from the reaction mixture using a known method, such as extraction, recrystallization or chromatography.

Method E

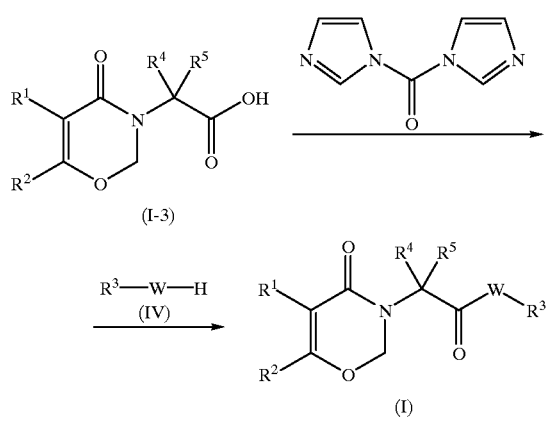

in which $R^1$, $R^2$, $R^4$, $R^5$ and W are as defined in general formula (I).

The compound of formula (I) can be obtained by reacting the compound of formula (I-3) with carbonyldiimidazole followed by treatment with the compound of formula (IV) or the salt thereof.

The reaction temperature is preferably from 0° C. to about 60° C. for the first process above, and from room temperature to about 100° C. or to the boiling point of the solvent for the second process.

The reaction time is usually from 0.5 to 24 hours.

The solvent used is not particularly limited so far as it is inert under the conditions of Method E, and the preferred examples of the solvent include halogenated hydrocarbon solvents such as carbon tetrachloride, chloroform or methylene chloride; hydrocarbon solvents such as toluene, xylene or mesitylene; ether solvents such as diethyl ether, tetrahydrofuran or dimethoxyethane; ketone solvents such as acetone or methyl ethyl ketone; and polar aprotic solvents such as acetonitrile, N,N-dimethylformamide or N,N-dimethylacetoamide.

The products of formula (I) can be isolated and purified from the reaction mixture using a known method, such as extraction, recrystallization or chromatography.

Method F

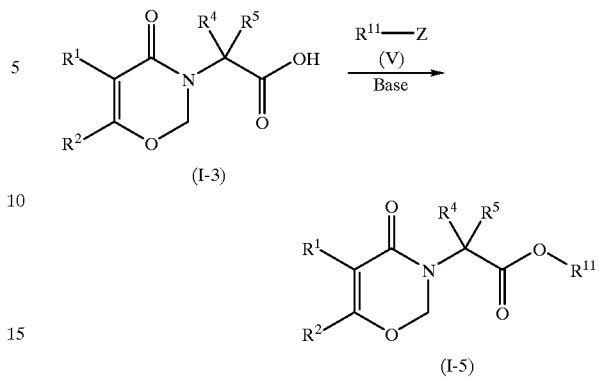

in which $R^1$, $R^2$, $R^4$ and $R^5$ are as defined in formula (I); $R^{11}$ is a primary or secondary lower alkyl group or an aralkyl group; Z is a halogen atom, a p-toluensulfonyloxy group, a methylsulfonyloxy group, a trifluoromethylsulfonyloxy group or a group which can be a good leaving group by the nucleophilic reaction as represented by formula $OSO_2OR^{11}$.

The compound of formula (I-5) can be obtained by reacting the compound of formula (I-3) with the compound of formula (V) in the presence of base.

The reaction temperature is preferably from room temperature to about 140° C. or to the boiling point of the solvent.

The solvent used is not particularly limited so far as it is inert under the conditions of Method F, and preferred examples of the solvent include polar aprotic solvents such as N,N-dimethylformamide, dimethylsulphoxide, acetonitrile or acetone; ether solvents such as tetrahydrofuran or dioxane; alcohols such as methanol or ethanol; and a mixture of water and the above-mentioned solvents.

Examples of base include inorganic carbonates such as potassium carbonate, potassium bicarbonate, sodium carbonate or sodium bicarbonate; inorganic bases such as sodium hydroxide or potassium hydroxide; sodium methoxide; and sodium hydride. The base can also be applied as a salt formed with the compound of formula (I-3), if required.

The product represented by general formula (I-5) can be isolated and purified from the reaction mixture using a known method, such as extraction, recrystallization or chromatography.

Method G

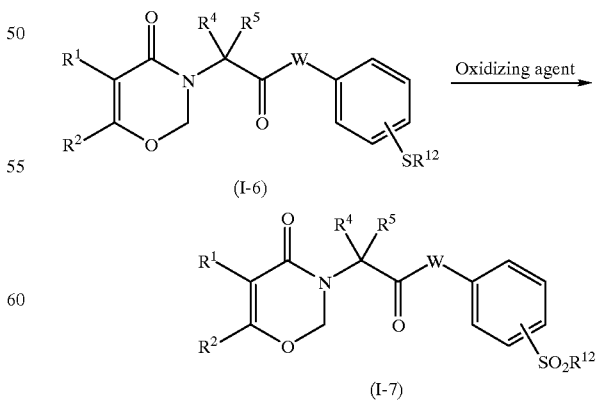

in which $R^1$, $R^2$, $R^3$, $R^4$, $R^5$ and W are as defined in general formula (I), and $R^{12}$ is a lower alkyl group.

The compound represented by general formula (I-7) can be obtained by oxidizing the compound of formula (I-6) with an adequate oxidizing agent.

Examples of the oxidizing agent include hydrogen peroxide, m-chloroperbenzoic acid, sodium metaperiodate, peracetic acid and potassium permaganate.

The reaction temperature is preferably from 0° C. to about 140° C. or to the boiling point of the solvent.

The solvent used is not particularly limited so far as it is inert under the conditions of Method G, and preferred examples of the solvent include halogenated hydrocarbon solvents such as 1,2-dichloroethane, carbon tetrachloride, chloroform or methylene chloride; methanol; acetic acid; water; and the mixture thereof.

The product represented by general formula (I-7) can be isolated and purified from the reaction mixture using a known method, such as extraction, recrystallization or chromatography.

Method H (I-8) → (I-9)

in which $R^1$, $R^2$, $R^3$, $R^4$ and $R^5$ are as in formula (I); $R^{13}$ is a primary or secondary lower alkyl group, a lower aralkenyl group or a lower alkynyl group; Z is as defined in general formula (V).

The compound of formula (I-9) can be obtained by reacting the compound of formula (I-8) with the compound of formula (VI) in the presence of base.

The reaction temperature is preferably from room temperature to about 140° C. or to the boiling point of the solvent.

The solvent used is not particularly limited so far as it is inert under the conditions of Method H, and preferred examples of the solvent include polar aprotic solvents such as N,N-dimethylformamide, dimethylsulphoxide, acetonitrile or acetone; ether solvents such as tetrahydrofuran or dioxane; alcohols such as methanol or ethanol; and a mixture of water and the above-mentioned solvents.

Examples of base include inorganic carbonates such as potassium carbonate, potassium bicarbonate, sodium carbonate or sodium bicarbonate; inorganic bases such as sodium hydroxide or potassium hydroxide; sodium methoxide; and sodium hydride.

The products of formula (I-9) can be isolated and purified from the reaction mixture using a known method, such as extraction, recrystallization or chromatography.

The compound of general formula (I) according to the present invention has strong herbicidal activities against many kinds of weeds and very weak phytotoxicities to useful crops.

When the compound represented by general formula (I) is used as a herbicide, it is mixed with an agriculturally and horticulturally acceptable carrier, diluent or additive and adjuvant by a known method while being formed into a formulation which is usually employed as agricultural chemicals, for example, wettable powder, granule, water-dispersible granule, emulsion concentrate or suspension concentrate. The compound may be mixed or used together with other agricultural chemicals, for example, fungicides, insecticides, miticides, herbicides, plant growth regulators, fertilizers and soil conditioners.

In particular, the mixed use with other herbicides can lead not only to reductions in doses, reductions in manpower, but also to the broadening of the herbicidal spectrum attributable to cooperative activities and further improved effects attributable to synergistic activities by the both agents.

The following can, for example, be mentioned as specific examples of other herbicides usable in a state such that they are mixed with the compounds of the present invention represented by general formula (I) (the term in parentheses denote common names unless otherwise defined).

Carbamate herbicides

Methyl 3,4-dichlorophenylcarbamate (Swep), isopropyl 3-chlorophenylcarbamate (Chlorproham), S-(4-chlorobenzyl)-diethylthiocarbamate (Benthiocarb), S-ethyl N,N-hexamethylenethiocarbamate (Molinate), S-(1-methyl-1-phenylethyl)-piperidine-1-carbothioate (Dimepiperate), S-benzyl N-ethyl-N-(1,2-dimethylpropyl) thiolcarbamate (Esprocarb), 3-(methoxycarbonyl)aminophenyl N-(3-methylphenyl)carbamate (Phenmedipham), ethyl 3-phenylcarbamoyloxyphenylcarbamate (Desmedipham), etc.

Urea herbicides 1-(α,α-Dimethylbenzyl)-3-(4-methylphenyl)urea (Dymron), 3-(3,4-dichlorophenyl)-1,1-dimethylurea (Diuron), 1,1-dimethyl-3-(α,α,α-trifluoro-m-tolyl)urea (Fluometuron), 3-[4-(4-chlorophenoxy)phenyl]-1,1-dimethylurea (Chloroxuron), 3-(3,4-dichlorophenyl)-1-methoxy-1-methylurea (Linuron), 3-(4-chlorophenyl)-1-methoxy-1-methylurea (Monolinuron), 3-(4-bromo-3-chlorophenyl)-1-methoxy-1-methylurea (Chlorbromuron), 1-(α,α-dimethylbenzyl)-3-(2-chlorobenzyl)urea (Code number JC-940), etc.

Haloacetamide herbicides 2-chloro-2',6'-diethyl-N-methoxymethylacetanilide (Alachlor), N-butoxymethyl-2-chloro-2',6'-diethylacetanilide (Butachlor), 2-chloro-2',6'-diethyl-N-(2-propoxyethyl) acetanilide (Pretilachlor), 2-chloro-N-isopropylacetanilide (Propachlor), etc.

Amide herbicides

3',4'-Dichloropropionanilide (Propanil), 2-bromo-N-(1,1-dimethylbenzyl)-3,3-dimethylbutanamide (Bromobutide), 2-benzothiazol-2-yloxy-N-methylacetanilide (Mefenacet), N,N-dimethyldiphenylacetamide (Diphenamid), etc.

Dinitrophenyl herbicides 4,6-dinitro-o-cresol (DNOC), 2-tert-butyl-4,6-dinitrophenol (Dinoterb), 2-sec-butyl-4,6-dinitrophenol (Dinoseb), N,N-diethyl-2,6-dinitro-4-trifluoromethyl-m-phenylenediamine (Dinitramine), α,α,α-trifluoro-2,6-dinitro-N,N-dipropyl-p-toluidine (Trifluralin), 4-methylsulfonyl-2,6-dinitro-N, N-dipropylaniline (Nitralin), N-(1-ethylpropyl)-2,6-dinitro-3,4-xylidine (Pendimethalin), etc.

Phenoxy herbicides 2,4-Dichlorophenoxyacetic acid (2,4-D), 2,4,5-trichlorophenoxyacetic acid (2,4,5-T), 4-chloro-o-tolyloxyacetic acid (MCPA), S-ethyl-(4-chloro-2-methylphenoxy)-ethanethioate (MCPA thioethyl), 4-(4-chloro-o-tolyloxy) butyric acid (MCPB), 4-(2,4-dichlorophenoxy) butyric acid (2,4-DB), 2-(4-chloro-o-tolyloxy) propionic acid (Mecoprop), 2-(2,4-dichlorophenoxy) propionic acid (Dichlorprop), (RS)-2-[4-(2,4-dichlorophenoxy)phenoxy]propionic acid (Diclofop) and its esters, (RS)-2-[4-(5-trifluoromethyl-2-pyridyloxy)phenoxy]propionic acid (Fluazifop) and its esters, 2-(2,4-dichloro-3-methylphenoxy)propionanilide (Clomeprop), S-ehtyl 4-chloro-2-methylphenoxy-thioacetate (Phenothiol), 2-(2-naphthoxy) propionanilide (Naproanilide), etc.

Carboxylic acid herbicides 2,2-Dichloropropionic acid (Dalapone), trichloroacetic acid (TCA), 2,3,6-trichlorobenzoic acid (2,3,6-TBA), 3,6-dichloro-o-anisic acid (Dicamba), 3-amino-2,5-dichlorobenzoic acid (Chloramben), etc.

Organophosphorus herbicides

O-Ethyl O-(2-nitro-5-methylphenyl)-N-sec-butyl-phosphoramidethioate (Butamifos), O,O-diisopropyl S-(2-benzenesulfonylaminoehtyl)phosphorodithioate (SAP), S-(2-methylpiperidin-1-yl) carbonylmethyl O,O-dipropyl-phosphorodithioate (Piperophos), etc.

Benzonitrile herbicides 2,6-Dichlorobenzonitrile (Dichlobenil), 3,5-dibromo-4-hydroxybenzonitrile (Bromoxynil), 4-hydroxy-3,5-diiodobenzonitrile (Ioxynil), etc.

Diphenylether herbicides 2,4-Dichlorophenyl 4-nitrophenyl ether (Nitrofen), 2,4,6-trichlorophenyl 4'-nitrophenyl ether (Chlornitrofen), 2,4-dichlorophenyl 3-methoxy4-nitro-phenyl ether (Chlomethoxyfen), methyl 5-(2,4-dichlorophenoxy)-2-nitrobenzoate (Bifenox), 4-nitrophenyl α,α,α-trifluoro-2-nitro-p-tolyl ether (Fluorodifen), 2-chloro-4-trifluoromethylphenyl 3-ethoxy-4-nitrophenyl ether (Oxyfluorfen), 5-(2-chloro-α,α,α-trifluoro-p-tolyloxy)-2-nitrobenzoic acid (Acifluorfen), etc.

Triazine herbicides

4-Amino-3-methyl-6-phenyl-1,2,4-triazin-5(4H)-one (Metamitron), 4-amino-6-tert-butyl-3-methylthio-1,2,4-triazin-5(4H)-one (Metribuzin), 2-chloro-4,6-bis-(ethylamino)-1,3,5-triazine (Simazine), 2-chloro-4-ethylamino-6-isopropylamino-1,3,5-triazine (Atrazin), 2,4-bis(ethylamino)-6-methylthio-1,3,5-triazine (Simetryn), 2,4-bis(isopropylamino)-6-methylthio-1,3,5-triazine (Prometryn), 2-(1,2-dimethylpropylamino)-4-ethylamino-6-methylthio-1,3,5-triazine (Dimethametryn), etc.

Sulfonylurea herbicides

2-Chloro-N-[4-methoxy-6-methyl-1,3,5-triazin-2-yl)aminocarbonyl]benzenesulfonamide (Chlorosulfuron), methyl 2-{[((4,6-dimethoxypyrimidin-2-yl)aminocarbonyl)aminosulfonyl]methyl}benzoate (Bensulfuron methy), ethyl 2-{[(4-chloro-6-methoxypyrimidin-2-yl)aminocarbonyl]aminosulfonyl}benzoate (Chlorimuron ethyl), etc.

Diazine herbicides 4-(2,4-Dichlorobenzoyl)-1,3-dimethylpyrazol-5-yl-p-toluenesulfonate (Pyrazolate), 1,3-dimethyl4-(2,4-dichlorobenzoyl)-5-phenacyloxypyrazole (Pyrazoxyfen), 1,3-dimethyl4-(2,4-dichloro-3-methyl-benzoyl)-5-(4-methylphenacyloxy)pyrazole (Benzofenap), etc.

Other herbicides 3,6-Dichloropyridine-2-carboxylic acid (Clopyralid), 4-amino-3,5,6-trichloropyridine-2-carboxylic acid (Picloram), 5-amino-4-chloro-2-phenyl-pyridazin-3(2H)-one (Chloridazon), 3-cyclohexyl-1,5,6,7-tetrahydrocyclopentenopyrimidine-2,4(3H)-dione (Lenacil), 5-bromo-3-sec-butyl-6-methyluracil (Bromacil), 3-tert-butyl-5-chloro-6-methyuracile (Terbacil), 3-isopropyl-(1 H)-2,1,3-benzothiadiazin-4(3H)-one-2,2-dioxide (Bentazone), N-1-naphthylphthalamic acid (Naptalam), etc.

As the agriculturally and horticulturally acceptable carriers or diluents used in the formulation of the compounds of this invention alone or in mixing with other herbicides, solid or liquid carriers usually used in agriculture may be used.

Examples of such solid carriers or diluents include clays represented by kaolinites, montmorillonites, illites, palygorskites, etc., more specifically pyrophyllite, attapulgite, sepiolite, kaolinite, bentonite, vermiculite, mica, talc, etc.; and other inorganic substances such as gypsum, calcium carbonate, dolomite, diatomaceus earth, magnesium line, phosphorus lime, zeolite, silicic anhydride, synthetic calcium silicate, etc.; organic substances of vegetable origin such as soybean flour, tobacco flour, walnut flour, wheat flour, wood flour, starch, crystalline cellulose, etc.; synthetic or natural polymers such as coumarone resin, petroleum resin, alkyd resin, polyvinyl chloride, polyalkylene glycol, ketone resin, ester gum, copal gum, dammar gum, etc.; waxes such as carnauba wax, beeswax, etc.; or urea and the like.

Examples of suitable liquid carriers or diluents include paraffin or naphthene hydrocarbons such as kerosene, mineral oil, spindle oil, white oil, etc.; aromatic hydrocarbons such as xylene, ethylbenzene, cumene, methylnaphthalene, etc.; chlorinated hydrocarbons such as trichloroethylene, monochlorobenzene, o-chlorotoluene, etc.; ethers such as dioxane, tetrahydrofuran, etc.; ketones such as acetone, methyl ethyl ketone, diisobutyl ketone, cyclohexanone, acetophenone, isophorone; esters such as ethyl acetate, amyl acetate, ethylene glycol acetate, diethylene glycol acetate, dibutyl maleate, diethyl succinate, etc.; alcohols such as methanol, n-hexanol, ethylene glycol, diethylene glycol, cyclohexanol, benzyl alcohol, etc.; ether alcohols such as ethylene glycol ethyl ether, diethylene glycol butyl ether, etc.; polar solvents such ass dimethylformamide, dimethyl sulfoxide, etc., or water.

In addition, surfactants and other auxiliary agents may be used for various purposes such as emulsification, dispersion, humidification, spreading, dilation, combination destruction control, stabilization of active ingredients, improvement of flowability, prevention of corrosion, prevention of freezing, etc., of the compounds of the invention.

As the surfactant, although one of nonionic, anionic, cationic and amphoteric surfactants may be used, nonionic and (or) anionic surfactants are usually used. Examples of suitable nonionic surfactants include addition polymerization products of ethylene oxide with higher alcohols such as lauryl alcohol, stearyl alcohol, oleyl alcohol, etc.; addition polymerization products of ethylene oxide with alkylnaphthols such as butylnaphthol, octylnaphthol, etc.; addition polymerization products of ethylene oxide with higher fatty acids such as palmitic acid, stearic acid, oleic acid, etc.; higher fatty acid esters of polyhydric alcohols such as sorbitan, and addition polymerization products of ethylene oxide therewith; etc.

As suitable anionic surfactants, there can be cited, for example, alkyl sulfate salts such as sodium laurylsulfate, amine salts of sulfuric acid ester of oleyl alcohol, etc., alkyl sulfonate salts such as sodium dioctyl sulfosuccinate, sodium 2-ethylhexylsulfonate, etc., arylsulfonate salts such as sodium isopropyl naphthalenesulfonate, sodium methylene bisnaphthalenesulfonate, sodium lignosulfonate, sodium dodecyl benzenesulfonate, etc., and the like.

Further, for the purpose of improving the properties of formulations, enhancement of effects, etc., the herbicides of this invention may be used in combination with polymers and other auxiliary agents such as casein, gelatin, albumin, glue, sodium alginate, carboxymethylcellulose, methylcellulose, hydroxyethylcellulose, polyvinyl alcohol, etc.

The above-described carriers or diluents and various auxiliary agents are used singly or in combination with others depending on the purpose taking into consideration forms of formulation, conditions of application, etc.

The contents of active ingredients in the various formulations of this invention thus prepared may vary widely depending on forms of formulation, and suitable content is within the range of usually 0.1 to 99% by weight, and preferably 1 to 80% by weight, which is most suitable.

Wettable powder contain active ingredient compounds in amounts of usually 25 to 90%, and the remainder solid carriers or diluents and dispersion wetting agents. If necessary, colloid protection agents, defoaming agents, etc. may be added thereto.

Granule contain, for example, active ingredient compounds in amounts of usually 1 to 35%, and the remainder may be solid carriers or diluents and surfactants. The active ingredient compounds may be mixed with solid carriers or diluents uniformly, or fixed to or adsorbed on the surfaces of solid carriers or diluents uniformly. It is preferred that the diameter of the granules be within the range of about 0.2 to 1.5 mm.

Emulsion concentrate contain, for example, active ingredient compounds of usually 5 to 30%, and in addition about 5 to 20% by weight of emulsifiers, the remainder being liquid carriers or diluents. If necessary, spreading agents and anticorrosive agents may be added thereto.

Suspension concentrate contain, for example, active ingredient compounds in amounts of usually 5 to 50%, and in addition 3 to 10% by weight of dispersion wetting agents, with the remainder being water. If necessary, protective colloid agents, preservatives, defoaming agents, etc. may be added thereto.

The compounds of this invention may be used as herbicides as they are or in any forms of formulation described above.

The herbicides of this invention may be applied in effective amounts to various places to be protected, for example, farm-lands such as paddy fields and upland, or non-crop lands, prior to germination of weeds or to weeds of various stages from after germination to growth period. The dose is generally, as amount of active ingredients, on the order of 0.1 to 10,000 g/ha, preferably 1 to 5,000 g/ha. The dose may be varied properly depending on the kind of objective weeds, their growth stages, places of application, weather, etc.

The compound of formula (I) and the herbicide provided by this invention have strong herbicidal activities against many kinds of weeds and very weak phytotoxicities to useful crops, as will be apparent from the test examples described later on.

For example, the compound of this invention exhibits excellent herbicidal effects at very low doses over a wide range of time from germination to and including the growth period of annual weeds such as *Echinochloa crus-galli, Cyperus difformis, Monochoria vaginalis, Rotala indica, Lindernia procumbens, Dopetrium junceum, Eleocharis acicularis,* and *Alisma canaliculatum,* and perennial weeds such as *Scirpus juncoides,* and *Cyperus serotinus,* while simultaneously being very safe towards paddy field rice plants. Another feature of the compound of the present invention is that when applied to soil or stem and leaves, it exhibits high herbicidal activities on various weeds which also cause problems in uplands to include perennial and annual Cyperaceous weeds such as *Cyperus rotundus, Cyperus esculontus, Cyperus brevifolius, Cyperus microiria,* and *Cyperus iria* and *Echinochloa crus-galli, Drigitaria sanguinalis, Setaria viridis, Poa annua, Sorghum halepense, Avena sativa,* and *Alopecurus myosuroides* as well as broad-leaved weeds such as *Polygonum lapathifolium, Amaranthus viridis,* and *Chenopodium album,* while simultaneously being very safe toward soybeans, cotton, sugar beets, maize, upland rice plants, wheat, etc.

Further, the compound according to the present invention can be used not only in paddy fields, and uplands, but also in orchards, mulberry fields, lawns, and non-crop lands.

In addition, when the compound according to the present invention is used in combination with other known agricultural chemicals having herbicidal activities, they exhibit complete herbicidal effects on weeds which are difficult to control with each of the compounds applied alone, and effectively control various weeds by synergistic herbicidal effects at doses at which a single compound is not effective. They are also very safe towards paddy field rice plants, soybeans, cotton, sugar beets, maize, upland rice plants, wheat, etc., so that they can provide herbicides which are very useful in agriculture.

EXAMPLES

Next, production of the compound of formula (I) and the intermediate compound of formula (II) will be described in more detail in the following examples.

Example 1

Preparation of Methyl 2-(N-methylenamino)-2-methylbutyrate (Compd. No. 2–15)

To methyl 2-amino-2-methylbutyrate (2.62 g) was dropped at room temperature 37% formalin (2.27 g), and the mixture was stirred for 4 h. Then the reaction mixture was dissolved in ether and washed with water. The organic phase was dried over magnesium sulfate, filtered and evaporated to get the captioned compound (2.80 g).

Example 2

Preparation of Methyl 2-methyl-2-(6-methyl-5-phenyl-2,3-dihydro-4-oxo-4H-1 3-oxazin-3-yl)-butyrate (Compd. No. 651)

To a mixture of 2,2,6-trimethyl-5-phenyl-4H-1,3-dioxin-4-one (2.18 g) and methyl 2-(N-methylenamino)-2-methylbutyrate (1.5 g) was added 20 ml of xylene, and the mixture was refluxed for 1 h. The solvent was evaporated and the residue was purified by chromatography on a silica gel column to get the captioned compound (2.4 g).

Example 3

Preparation of 2-methyl-2-(6-methyl-5-phenyl-2 3-dihydro-4-oxo-4H-1,3-oxazin-3-yl)-butyric Acid (Compd. No. 650)

To a solution of methyl 2-methyl-2-(6-methyl-5-phenyl-2, 3-dihydro-4-oxo-4 H-1,3-oxazin-3-yl)-butyrate (1.91 g) in 20 ml of ethanol was added at room temperature 30 ml of aq. NaOH (0.3N). After stirring for 24 h, ethanol was evaporated, and the mixture was acidified by hydrochloric acid. The precipitate was filtered off and dried to get the captioned compound (1.36 g).

Example 4

Preparation of Benzyl 2-(N-methylenamino)-2-methylpropionate (Compd. No. 2–10)

To benzyl 2-amino-2-methylbutyrate (12.96 g) was dropped at room temperature 37% formalin (7.62 g), and the mixture was stirred for 4 h. The reaction mixture was dissolved in ether and washed with water. The organic phase was dried over magnesium sulfate, filtered and evaporated to get the captioned compound (13.7 g).

Example 5

Preparation of Benzyl 2-methyl-2-(6-methyl-5-phenyl-2,3-dihydro-4-oxo-4H-1,3-oxazin-3-yl)-propionate (Compd. No. 645)

To a mixture of 2,2,6-trimethyl-5-phenyl-4H-1,3-dioxin-4-one (13.97 g) and benzyl 2-(N-methylenamino)-2-methylpropionate (13.8 g) was added 130 ml of xylene, and the mixture was refluxed for 2 h. The solvent was evaporated and the residue was purified by chromatography on a silica gel column to get the captioned compound (21.1 g).

Example 6

Preparation of 2-methyl-2-(6-methyl-5-phenyl-2,3-dihydro-4-oxo-4H-1 3-oxazin-3-yl)-propionic Acid (Compd. No. 634)

To a solution of benzyl 2-methyl-2-(6-methyl-5-phenyl-2,3-dihydro-4-oxo-4H-1,3-oxazin-3-yl)-propionate (21.1 g)

in 100 ml of ethanol was added 1 g of 5% Pd on carbon and hydrogenated at room temperature under normal pressure. After ethanol was evaporated, saturated aq. sodium bicarbonate was added to the mixture and the catalyst was filtered off. The filtrate was acidified by hydrochloric acid. The precipitate was filtered off and dried to get the captioned compound (10.8 g).

Example 7

Preparation of Ethyl 2-methyl-2-(6-methyl-5-phenyl-2,3-dihydro-4-oxo-4H-1,3-oxazin-3-yl)-propionate (Compd. No. 636)

To a mixture of 2-methyl-2-(6-methyl-5-phenyl-2,3-dihydro-4-oxo-4H-1,3-oxazin-3-yl)-propionic acid (0.83 g) and potassium carbonate (0.45 g) in 4 ml of dimethylformamide (DMF) was added ethyl iodide (0.56 g), and the mixture was stirred at 60° C. for 5 h. The reaction mixture was poured into water and extracted with ethyl acetate. The organic layer was washed with brine, dried over magnesium sulfate and evaporated. The residue was purified by chromatography on a silica gel column to get the captioned compound (0.87 g).

Example 8

Preparation of 3,5-dichlorophenyl 2-methyl-2-(6-methyl-5-phenyl-2 3-dihydro-4-oxo-4H-1,3-oxazin-3-yl)-propionate (Compd. No. 506)

To a suspension of 2-methyl-2-(6-methyl-5-phenyl-2,3-dihydro-4-oxo-4H-1,3-oxazin-3-yl)-propionic acid (1.1 g) in 14 ml of $CCl_4$—$CH_2Cl_2$ (1:1) was added triphenylphosphin (1.38 g), then the mixture was refluxed for 40 min. The reaction mixture was ice-cooled and 3,5-dichlorophenol (0.65 g) and triethylamine (0.4 g) were slowly added, then it was stirred at room temperature for 1 h. After evaporation of the solvent, the residue was dissolved in ethyl acetate. The insolubles were filtered off and the filtrate was evaporated. The residue was purified by chromatography on a silica gel column to get the captioned compound (0.7 g).

Example 9

Preparation of N-phenyl-2-methyl-2-(6-methyl-5-phenyl-2 3-dihydro-4-oxo-4H-1,3-oxazin-3-yl)-propanamide (Compd. No. 1)

To a suspension of 2-methyl-2-(6-methyl-5-phenyl-2,3-dihydro-4-oxo-4H-1,3-oxazin-3-yl)-propionic acid (0.83 g) in 10.4 ml of $CCl_4$—$CH_2Cl_2$ (1:1) was added triphenylphosphin (1.04 g), then the mixture was refluxed for 40 min. The reaction mixture was ice-cooled and aniline (0.28 g) and triethylamine (0.3 g) were slowly added, then it was stirred at room temperature for 1 h. After evaporation of the solvent, the residue was dissolved in ethyl acetate. The insolubles were filtered off and the filtrate was evaporated. The residue was purified by chromatography on a silica gel column to get the captioned compound (0.58 g).

Example 10

Preparation of N-(3 5-dichlorophenyl)-2-methyl-2-(6-methyl-5-phenyl-2,3-dihydro-4-oxo-4H-1,3-oxazin-3-yl)-propanamide (Compd. No. 27)

The captioned compound (1.05 g) was prepared in the same manner as described in Example 9 except 3,5-dichloroaniline was used as a starting material.

Example 11

Preparation of N-(3-trifluoromethylphenyl)-2-methyl-2-(6-methyl-5-phenyl-2 3-dihydro-4-oxo-H-1,3-oxazin-3-yl)-propanamide (Compd. No. 93)

The captioned compound (0.72 g) was prepared in the same manner as described in Example 9 except 3-trifluoromethylaniline was used as a starting material.

Example 12

Preparation of N-isopropyl-2-methyl-2-(6-methyl-5-phenyl-2 3-dihydro-4-oxo-4H-1,3-oxazin-3-yl)-propanamide (Compd. No. 604)

To a solution of 2-methyl-2-(6-methyl-5-phenyl-2,3-dihydro-4-oxo-4H-1,3-oxazin-3-yl)-propionic acid (0.83 g) in 6 ml of tetrahydrofuran (THF) was added carbonyldiimidazole (0.59 g). After stirring at room temperature for 30 min., isopropylamine (0.23 g) was added and the reaction mixture was stirred at 60° C. for 5 h. Then it was poured into water and extracted with ethyl acetate. The organic layer was washed with brine, dried over magnesium sulfate and evaporated. The residue was purified by chromatography on a silica gel column to get the captioned compound (0.38 g).

Example 13

Preparation of N-(3,5-dichlorophenyl)-N-methyl-2-methyl-2-(6-methyl-5-phenyl-2,3-dihydro-4-oxo-4H-1,3-oxazin-3-yl)-propanamide (Compd. No. 302)

A solution of N-(3,5-dichlorophenyl)-2-methyl-2-(6-methyl-5-phenyl-2,3-dihydro-4-oxo-4H-1,3-oxazin-3-yl)-propanamide (0.6 g) in 2 ml of DMF was cooled in an ice bath and 60% sodium hydride in oil (0.06 g) was added. The mixture was stirred at room temperature for 30 min. and subsequently methyl iodide (0.31 g) was added and the mixture was stirred at room temperature for 5 h. Then the reaction mixture was poured into water and extracted with ethyl acetate. The organic layer was washed with brine, dried over magnesium sulfate and evaporated. The residue was purified by chromatography on a silica gel column to get the captioned compound (0.51 g).

Example 14

Preparation of N-[4-(methylsulfonyl)phenyl]-2-methyl-2-(6-methyl-5-phenyl-2,3-dihydro-4-oxo-4H-1,3-oxazin-3-yl)-propanamide (Compd. No. 151)

A solution of N-(4-methylthiophenyl)-2-methyl-2-(6-methyl-5-phenyl-2,3-dihydro-4-oxo-4H-1,3-oxazin-3-yl)-propanamide (0.6 g) in 12 ml of 1,2-dichloroethane was cooled in an ice bath and 70% methachloroperbenzoic acid (0.8 g) was added. After stirring at room temperature for. 24 h, the reaction mixture was washed with saturated aq. sodium bicarbonate, dried over magnesium sulfate and evaporated. The residue was purified by chromatography on a silica gel column to get the captioned compound (0.5 g).

Example 15

Preparation of N-[2-fluoro-5-(trifluoromethyl) phenyl]-2-methyl-2-(6-methyl-5-phenyl-2,3-dihydro-4-oxo-4H-1,3-oxazin-3-yl)-propanamide (Compd. No. 363)

The captioned compound (0.93 g) ) was prepared in the same manner as described in Example 9, except 2-fluoro-5-(trifluoromethyl)aniline was used as a starting material.

The physical properties of the various compounds prepared by the similar methods as described in the Examples are shown in Tables 1 to 6 previously mentioned, and $^1$H-NMR data of those compounds are shown in Tables 7 and 8 below.

TABLE 7

| Compd. No. | $^1$H-NMR (300MHz) δ(ppm) Solvent CDCl$_3$ TMS = 0 ppm |
|---|---|
| 1 | 1.72(s, 6H), 1.95(s, 3H), 5.30(s, 2H), 7.07(t, 1H), 7.23–7.38(m, 7H), 7.49(d, 2H), 8.39(brs, 1H) |
| 2 | 1.69(s, 6H), 1.96(s, 3H), 5.32(s, 2H), 6.95–7.3(m, 8H), 8.13(brs, 1H), 8.25–8.34(m, 1H) |
| 3 | 1.70(s, 6H), 1.95(s, 3H), 5.30(s, 2H), 6.70–6.80(m, 1H), 7.06–7.52(m, 8H), 8.57(brs, 1H) |
| 4 | 1.71(s, 6H), 1.95(s, 3H), 5.30(s, 2H), 6.91–7.46(m, 9H), 8.41(brs, 1H) |
| 5 | 1.68(s, 6H), 1.96(s, 3H), 5.34(s, 2H), 7.00(ddd, 1H), 7.20–7.37(m, 7H), 8.38(dd, 1H), 8.42(brs, 1H) |
| 6 | 1.70(s, 6H), 1.95(s, 3H), 5.30(s, 2H), 7.01–7.07(m, 1H), 7.16–7.41(m, 7H), 7.65(t, 1H), 8.51(brs, 1H) |
| 7 | 1.70(s, 6H), 1.95(s, 3H), 5.30(s, 2H), 7.20–7.48(m, 9H), 8.50(brs, 1H) |
| 9 | 1.70(s, 6H), 1.95(s, 3H), 5.30(s, 2H), 7.10–7.42(m, 8H), 7.78(m, 1H), 8.50(brs, 1H) |
| 12 | 1.69(s, 6H), 1.95(s, 3H), 5.29(s, 2H), 6.99(t, 1H), 7.22–7.47(m, 7H), 7.94(t, 1H), 8.44(brs, 1H) |
| 14 | 1.68(s, 6H), 1.96(s, 3H), 5.32(s, 2H), 6.855(m, 1H), 7.02(m, 1H), 7.22–7.37(m, 5H), 8.05(m, 1H), 8.19(brs, 1H) |
| 15 | 1.68(s, 6H), 1.96(s, 3H), 5.32(s, 2H), 6.77–6.92(m, 2H), 7.20–7.38(m, 5H), 8.05(brs, 1H), 8.15–8.26(m, 1H) |
| 16 | 1.67(s, 6H), 1.96(s, 3H), 5.32(s, 2H), 6.64–6.73(m, 1H), 6.94–7.04(m, 1H), 7.21–7.37(m, 5H), 8.12–8.24(m, 2H) |
| 17 | 1.71(s, 6H), 1.94(s, 3H), 5.29(s, 2H), 6.91(m, 2H), 7.15(m, 1H), 7.26–7.39(m, 5H), 7.93(brs, 1H) |
| 18 | 1.69(s, 6H), 1.95(s, 3H), 5.30(s, 2H), 6.98–7.10(m, 2H), 7.22–7.39(m, 5H), 7.54–7.63(m, 1H), 8.54(brs, 1H) |
| 19 | 1.68(s, 6H), 1.95(s, 3H), 5.29(s, 2H), 6.50(tt, 1H), 7.11(m, 2H), 7.22–7.40(m, 5H), 8.67(brs, 1H) |
| 21 | 1.69(s, 6H), 1.95(s, 3H), 5.29(s, 2H), 7.22–7.40(m, 5H), 8.16(brs, 1H) |
| 22 | 1.67(s, 6H), 1.97(s, 3H), 5.34(s, 2H), 7.16–7.37(m, 7H), 8.34(dd, 1H), 8.51(brs, 1H) |
| 23 | 1.66(s, 6H), 1.96(s, 3H), 5.33(s, 2H), 7.20–7.38(m, 7H), 8.35(d, 1H), 8.37(brs, 1H) |
| 24 | 1.67(s, 6H), 1.96(s, 3H) 5.33(s, 2H), 6.98(dd, 1H), 7.21–7.37(m, 6H), 8.41(brs, 1H), 8.51(d, 1H) |
| 26 | 1.69(s, 6H), 1.95(s, 3H), 5.30(s, 2H), 7.21–7.39(m, 7H), 7.75–7.78(m, 1H), 8.62(brs, 1H) |
| 27 | 1.69(s, 6H), 1.96(s, 3H), 5.29(s, 2H), 7.05(t, 1H), 7.22–7.40(m, 5H), 7.48(d, 1H), 8.66(brs, 1H) |
| 28 | 1.67(s, 6H), 1.95(s, 3H), 5.29(s, 2H), 7.22–7.40(m, 5H), 7.62(s, 2H), 8.72(brs, 1H) |
| 30 | 1.67(s, 6H), 1.96(s, 3H), 5.31(s, 2H), 7.05–7.12(m, 2H), 7.20–7.37(m, 5H), 8.11(brs, 1H), 8.21–8.28(m, 1H) |
| 31 | 1.69(s, 6H), 1.95(s, 3H), 5.30(s, 2H), 7.03(t, 1H), 7.21–7.40(m, 6H), 7.69(dd, 1H), 8.51(brs, 1H) |
| 34 | 1.71(s, 6H), 1.95(s, 3H), 2.22(s, 3H), 5.31(s, 2H), 7.03(t, 1H), 7.11–7.39(m, 7H), 7.84(d, 1H), 8.00(brs, 1H) |
| 35 | 1.70(s, 6H), 1.94(s, 3H), 2.31(s, 3H), 5.29(s, 2H), 6.89(d, 1H), 7.13–7.42(m, 8H), 8.32(brs, 1H) |
| 36 | 1.67(s, 6H), 1.92(s, 3H), 2.27(s, 3H), 5.27(s, 2H), 7.07(d, 2H), 7.21–7.39(m, 7H), 8.25(brs, 1H) |
| 39 | 1.72(s, 6H), 1.95(s, 3H), 5.32(s, 2H), 6.85(d, 1H), 7.02(d, 1H), 7.23–7.38(m, 5H), 7.71(brs, 1H), 7.94(brs, 1H) |
| 40 | 1.76(s, 6H), 1.94(s, 3H), 2.23(s, 6H), 5.33(s, 2H), 7.01–7.10(m, 3H), 7.24–7.39(m, 5H), 7.74(brs, 1H) |
| 42 | 1.70(s, 6H), 1.94(s, 3H), 2.26(s, 6H), 5.30(s, 2H), 6.72(brs, 1H), 7.14(brs, 2H), 7.23–7.38(m, 5H), 8.27(brs, 1H) |
| 46 | 1.67(s, 6H), 1.96(s, 3H), 2.46(s, 3H), 5.33(s, 2H), 7.21–7.38(m, 6H), 8.30–8.37(m, 1H), 8.21(d, 1H), 8.45(brs, 1H) |
| 49 | 1.21(t, 3H), 1.71(s, 6H), 1.94(s, 3H), 2.61(q, 2H), 5.30(s, 2H), 6.92(d, 1H), 7.16–7.43(m, 8H), 8.34(brs, 1H) |
| 54 | 1.22(d, 6H), 1.72(s, 6H), 1.95(s, 3H), 2.87(sep, 1H), 5.30(s, 2H), 6.95(m, 1H), 7.17–7.38(m, 7H), 7.42(t, 1H), 8.34(brs, 1H) |
| 63 | 1.69(s, 6H), 1.96(s, 3H), 3.81(s, 3H), 5.33(s, 2H), 6.80–7.04(m, 3H), 7.21–7.36(m, 5H), 8.34(dd, 1H), 8.48(brs, 1H) |
| 64 | 1.69(s, 6H), 1.94(s, 3H), 3.77(s, 3H), 5.28(s, 2H), 6.62(dd, 1H), 6.92(dd, 1H), 7.16(t, 1H), 7.21–7.37(m, 6H), 8.37(brs, 1H) |
| 65 | 1.70(s, 6H), 1.94(s, 3H), 3.77(s, 3H), 5.29(s, 2H), 6.82(d, 2H), 7.22–7.44(m, 7H), 8.23(brs, 1H) |
| 72 | 1.66(s, 6H), 1.94(s, 3H), 5.29(s, 2H), 7.22–7.40(m, 5H), 7.44(s, 2H), 8.38(brs, 1H) |
| 73 | 1.68(s, 6H), 1.95(s, 3H), 5.29(s, 2H), 7.22–7.40(m, 5H), 7.66(s, 2H), 8.41(brs, 1H) |
| 88 | 1.68(s, 6H), 1.94(s, 3H), 5.28(s, 2H), 6.72(dd, 1H), 6.99(dd, 2H), 7.07(t, 1H), 7.20–7.40(m, 10H), 8.37(brs, 1H) |
| 92 | 1.65(s, 6H), 1.96(s, 3H), 5.31(s, 2H), 7.11–7.36(m, 6H), 7.48–7.60(m, 2H), 8.23(brs, 1H), 8.37(d, 1H) |
| 93 | 1.72(s, 6H), 1.96(s, 3H), 5.31(s, 2H), 7.21–7.42(m, 7H), 7.65(d, 1H), 7.85(brs, 1H), 8.64(brs, 1H) |
| 94 | 1.71(s, 6H), 1.96(s, 3H), 5.31(s, 2H), 7.21–7.39(m, 5H), 7.53, 7.62(ABq, 4H), 8.73(brs, 1H) |
| 95 | 1.65(s, 6H), 1.97(s, 3H), 5.32(s, 2H), 7.22–7.36(m, 5H), 7.41(brd, 1H), 7.69(brd, 1H), 8.41(brs, 1H), 8.86(brs, 1H) |
| 96 | 1.68(s, 6H), 1.96(s, 3H), 5.32(s, 2H), 7.21–7.37(m, 5H), 7.49(brs, 1H), 7.96(brs, 1H), 8.92(brs, 1H) |
| 102 | 1.67(s, 6H), 1.95(s, 3H), 5.32(s, 2H), 6.40(t, 1H), 6.99–7.10(m, 2H), 7.16–7.36(m, 6H), 8.40(dd, 1H), 8.45(brs, 1H) |
| 103 | 1.70(s, 6H), 1.95(s, 3H), 5.30(s, 2H), 6.50(t, 1H), 6.80–6.83(m, 1H), 7.19–7.39(m, 7H), 7.50(brs, 1H), 8.53(brs, 1H) |
| 104 | 1.70(s, 6H), 1.95(s, 3H), 5.30(s, 2H), 6.43(t, 1H), 7.04, 7.48(ABq, 4H), 7.22–7.39(m, 5H), 8.46(brs, 1H) |
| 110 | 1.67(s, 6H), 1.94(s, 3H), 5.29(s, 2H), 6.90(m, 1H), 7.20–7.37(m, 7H), 7.57(brs, 1H), 8.57(brs, 1H) |
| 123 | 1.65(s, 6H), 1.94(s, 3H), 5.31(s, 2H), 7.21–7.36(m, 7H), 7.57–7.65(m, 1H), 7.87(brs, 1H), 8.64(brs, 1H) |
| 124 | 1.71(s, 6H), 1.96(s, 3H), 5.30(s, 2H), 7.20–7.39(m, 5H), 7.56, 7.63(ABq, 4H), 8.90(brs, 1H) |
| 127 | 1.67(s, 6H), 1.99(s, 3H), 5.39(s, 2H), 7.12(ddd, 1H), 7.18–7.34(m, 5H), 7.61(t, 1H), 8.19(dd, 1H), 8.81(dd, 1H), 11.01(brs, 1H) |
| 128 | 1.76(s, 6H), 1.96(s, 3H), 5.32(s, 2H), 7.21–7.45(m, 6H), 7.85–7.92(m, 2H), 8.33–8.37(m, 1H), 8.74(brs, 1H) |
| 129 | 1.71(s, 6H), 1.96(s, 3H), 5.32(s, 2H), 7.20–7.40(m, 5H), 7.67, 8.15(ABq, 4H), 9.06(brs, 1H) |
| 131 | 1.69(s, 6H), 1.98(s, 3H), 5.35(s, 2H), 7.22–7.38(m, 5H), 8.64(t, 1H), 8.67(d, 2H), 9.25(brs, 1H) |
| 135 | 1.68(s, 6H), 1.96(s, 3H), 3.84(s, 3H), 5.42(s, 2H), 7.02(ddd, 1H), 7.18–7.35(m, 5H), 7.49(ddd, 1H), 7.98(dd, 1H), 8.71(dd, 1H), 11.52(brs, 1H) |
| 137 | 1.65(s, 6H), 1.92(s, 3H), 3.85(s, 3H), 5.28(s, 2H), 7.20–7.35(m, 5H), 7.57, 7.92(ABq, 4H), 8.65(brs, 1H) |
| 138 | 1.37(t, 3H), 1.69(s, 6H), 1.95(s, 3H), 4.35(q, 2H), 5.31(s, 2H), 7.20–7.38(m, 6H), 7.74(d, 1H), 7.88(dd, 1H), 7.99(brs, 1H), 8.39(brs, 1H) |
| 141 | 1.69(s, 6H), 1.95(s, 3H), 3.77(s, 3H), 4.62(s, 2H), 5.29(s, 2H), 6.65(dd, 1H), 7.01(d, 1H), 7.14–7.38(m, 7H), 8.41(brs, 1H) |
| 144 | 1.58(d, 3H), 1.68(s, 6H), 1.94(s, 3H), 3.71(s, 3H), 4.77(q, 1H), 5.28(s, 2H), 6.60(dd, 1H), 7.04(d, 1H), 7.12–7.38(m, 7H), 8.39(brs, 1H) |
| 146 | 1.69(s, 6H), 1.96(s, 3H), 2.26(s, 3H), 5.36(s, 2H), 7.01(t, 1H), 7.20–7.35(m, 5H), 7.45(dd, 1H), 8.38(dd, 1H), 9.08(brs, 1H) |
| 147 | 1.71(s, 6H), 1.95(s, 3H), 2.47(s, 3H), 5.30(s, 2H), 6.94–6.99(m, 1H), 7.16–7.39(m, 7H), 7.56(brs, 1H), 8.39(brs, 1H) |
| 148 | 1.69(s, 6H), 1.94(s, 3H), 2.44(s, 3H), 5.29(s, 2H), 7.18–7.48(m, 9H), 8.38(brs, 1H) |
| 149 | 1.67(s, 6H), 1.96(s, 3H), 2.59(s, 3H), 5.43(s, 2H), 7.16(t, 1H), 7.25–7.38(m, 5H), 7.56(t, 1H), 7.85(dd, 1H), 8.30(d, 1H), 9.99(d, 1H) |
| 151 | 1.67(s, 6H), 1.95(s, 3H), 2.99(s, 3H), 5.31(s, 2H), 7.20–7.40(m, 5H), 7.67, 7.78(ABq, 4H), 8.79(brs, 1H) |
| 152 | 1.65(s, 6H), 1.94(s, 3H), 5.32(s, 2H), 6.5–6.6(m, 1H), 6.7–6.8(m, 2H), 7.1–7.4(m, 7H) |
| 155 | 1.70(s, 6H), 1.96(s, 3H), 2.59(s, 3H), 5.32(s, 2H), 7.21–7.42(m, 6H), 7.66(dd, 1H), 7.79–7.86(m, 1H), 8.01–8.04(m, 1H), 8.42(brs, 1H) |
| 187 | 1.10(t, 3H), 1.70(s, 6H), 2.23(s, 3H), 5.30(s, 2H), 7.0–7.7(m, 9H), 8.51(brs, 1H) |
| 204 | 1.12(t, 3H), 1.73(s, 6H), 2.22(q, 2H), 5.33(s, 2H), 7.2–7.9(m, 9H), 8.64(brs, 1H) |
| 211 | 0.88(t, 3H), 1.4–1.65(m, 2H), 1.71(s, 6H), 2.29(t, 2H), 5.31(s, 2H), 7.0–7.7(m, 9H), 8.52(brs, 1H) |
| 214 | 1.71(s, 6H), 1.93(s, 3H), 5.33(s, 2H), 7.04–7.17(m, 3H), 7.25–7.35(m, 4H), 7.49(d, 2H), 8.37(brs, 1H) |
| 215 | 1.69(s, 6H), 1.94(s, 3H), 5.32(s, 2H), 7.01–7.24(m, 4H), 7.24–7.35(m, 3H), 7.64(t, 1H), 8.48(brs, 1H) |
| 220 | 1.67(s, 6H), 1.94(s, 3H), 5.32(s, 2H), 7.04(t, 1H), 7.04–7.18(m, 2H), 7.26–7.31(m, 2H), 7.47(d, 2H), 8.60(brs, 1H) |
| 298 | 1.59(s, 6H), 1.74(s, 3H), 3.19(s, 3H), 4.20(brs, 2H), 7.14–7.20(m, 2H), 7.26–7.42(m, 8H) |

TABLE 7-continued

| Compd. No. | ¹H-NMR (300MHz) δ(ppm) Solvent CDCl₃ TMS = 0 ppm |
|---|---|
| 302 | 1.57(s, 6H), 1.82(s, 3H), 3.21(s, 3H), 4.66(brs, 2H), 7.15(d, 2H), 7.26–7.40(m, 6H) |
| 339 | 1.66(s, 6H), 1.96(s, 3H), 5.31(s, 2H), 7.22–7.37(m, 5H), 7.93(m, 1H), 8.90(brs, 1H) |
| 341 | 1.72(s, 6H), 1.96(s, 3H), 5.30(s, 2H), 6.86(m, 1H), 7.14(m, 1H), 7.25–7.40(m, 5H), 8.09(brs, 1H) |
| 342 | 1.66(s, 6H), 1.95(s, 3H). 5.31(s, 2H), 6.93(m, 1H), 7.21–7.38(m, 5H), 8.11(brs, 1H), 8.26(m, 1H) |
| 343 | 1.72(s, 6H), 1.95(s, 3H), 5.29(s, 2H), 6.71(m, 2H), 7.23–7.40(m, 5H), 7.93(brs, 1H) |
| 344 | 1.65(s, 6H), 1.96(s, 3H), 5.30(s, 5H), 7.18–7.40(m, 5H), 8.01–8.14(m, 1H), 8.19(brs, 1H) |
| 345 | 1.70(s, 6H), 1.95(s, 3H), 5.29(s, 2H), 6.76–6.87(m, 1H), 7.24–7.40(m, 5H), 8.03(brs, 1H) |
| 346 | 1.70(s, 6H), 1.95(s, 3H), 5.29(s, 2H), 6.94(m, 1H), 7.25–7.40(m, 5H), 8.19(brs, 1H) |
| 348 | 1.66(s, 6H), 1.95(s, 3H), 5.32(s, 2H), 7.21–7.36(m, 5H), 7.43(s, 1H), 8.38(brs, 1H), 8.63(s, 1H) |
| 349 | 1.64(s, 6H), 1.96(s, 3H), 5.31(s, 2H), 7.20–7.36(m, 5H), 8.49(brs, 1H), 8.62(s, 1H) |
| 350 | 1.67(s, 6H), 1.96(s, 3H), 5.32(s, 2H), 6.95–7.00(m, 2H), 7.22–7.37(m, 5H), 8.17(brs, 1H), 8.39–8.43(m, 1H) |
| 353 | 1.67(s, 6H), 1.96(s, 3H), 5.31(s, 2H), 7.20–7.37(m, 8H), 8.13(brs, 1H), 8.21(t, 1H) |
| 354 | 1.70(s, 6H), 1.96(s, 3H), 5.29(s, 2H), 7.24–7.40(m, 5H), 8.25(brs, 1H) |
| 356 | 1.30(s, 18H), 1.72(s, 6H), 1.95(s, 3H), 5.31(s, 2H), 7.15(m, 1H), 7.23–7.38(m, 7H), 8.26(brs, 1H) |
| 357 | 1.68(s, 6H), 1.95(s, 3H), 2.29(s, 3H), 5.32(s, 2H), 6.79(m, 1H), 6.88–6.96(m, 1H), 7.22–7.38(m, 5H), 8.06(brs, 1H), 8.13(dd, 1H) |
| 361 | 1.68(s, 6H), 1.95(s, 3H), 2.49(s, 3H), 5.29(s, 2H), 7.23–7.39(m, 5H), 7.73(s, 2H), 8.46(brs, 1H) |
| 362 | 1.67(s, 6H), 1.97(s, 3H), 5.32(s, 2H), 7.17–7.38(m, 7H), 8.22(brs, 1H), 8.52(t, 1H) |
| 363 | 1.69(s, 6H), 1.96(s, 3H), 5.33(s, 2H), 7.15(s, 1H), 7.21–7.38(m, 6H), 8.31(brd, 1H) 8.71(brs, 1H) |
| 364 | 1.70(s, 6H), 1.95(s, 3H), 5.31(s, 2H), 7.10(t, 1H), 7.22–7.40(m, 5H), 7.65(m, 1H), 7.79(dd, 1H), 8.61(brs, 1H) |
| 365 | 1.69(s, 6H), 1.95(s, 3H), 5.31(s. 2H), 7.20–7.40(m, 6H), 7.64(dd, 1H), 7.86(d, 3H), 8.68(brs, 1H) |
| 369 | 1.66(s, 6H), 1.93(s, 3H), 5.28(s, 2H), 6.4–6.6(m, 1H), 6.84(brs, 1H), 6.9–7.4(m, 11H), 8.42(brs, 1H) |
| 370 | 1.68(s, 6H), 1.94(s, 3H), 5.30(s, 2H), 6.84(s, 1H), 7.09(dd, 1H), 7.2–7.4(m, 5H), 7.63(d, 1H), 8.23(brs, 1H) |
| 371 | 1.35(d, 6H), 1.67(s, 6H), 1.96(s, 3H), 4.53(sep, 1H), 5.32(s, 2H), 7.09(d, 1H), 7.2–7.4(m, 5H), 8.10(d, 1H), 8.10(brs, 1H) |
| 376 | 1.65(s, 6H), 1.94(s, 3H), 5.32(s, 2H), 7.10(dd, 1H), 7.21–7.36(m, 5H), 7.73(m, 1H), 8.15(dd, 1H), 8.72(brs, 1H) |
| 506 | 1.66(s, 6H), 1.94(s, 3H), 5.31(s, 2H), 7.07(d, 2H), 7.20(t, 1H), 7.23–7.41(m, 5H) |
| 600 | 1.59(s, 6H), 1.92(s, 3H), 5.26(s, 2H), 7.06(brs, 2H), 7.2–7.4(m, 4H), 7.62(brs, 1H) |
| 604 | 1.13(d, 6H), 1.61(brs, 6H), 1.92(s, 3H), 4.03(sep, 1H), 5.24(s, 2H), 5.87(d, 1H), 7.20–7.38(m, 5H) |
| 606 | 0.89(d, 6H), 1.61(s, 6H), 1.7–1.9(m, 1H), 1.92(s, 3H), 3.06(t, 2H), 5.25(s, 2H), 6.28(brs, 1H), 7.2–7.4(m, 4H) |
| 608 | 1.33(s, 9H), 1.57(s, 6H), 1.91(s, 3H), 5.23(s, 2H), 5.91(brs, 1H), 7.22–7.38(m, 5H) |
| 611 | 1.48(d, 3H), 1.61(s, 3H), 1.62(s, 3H), 1.90(s, 3H), 5.09(dq, 1H), 5.19, 5.23(ABq, 2H), 6.38(d, 1H), 7.19–7.39(m, 10H) |
| 612 | 1.60(s, 6H), 1.68(s, 6H), 1.91(s, 3H), 5.21(s, 2H), 6.46(brs, 1H), 7.18–7.42(m, 10H) |
| 613 | 1.54(s, 6H), 1.91(s, 3H), 2.80(t, 2H), 3.50(q, 2H), 5.19(s, 2H), 6.18(brt, 1H), 7.16–7.38(m, 10H) |
| 624 | 1.59(s, 6H), 1.92(s, 3H), 3.04(brs, 6H), 5.20(s, 2H), 7.2–7.4(m, 5H) |
| 634 | 1.59(s, 6H), 1.92(s, 3H), 5.27(s, 2H), 722–7.38(m, 5H) |
| 635 | 1.55(s, 6H), 1.92(s, 3H), 5.27(s, 2H), 7.20–7.37(m, 5H) |
| 636 | 1.22(t, 3H), 1.55(s, 6H), 1.91(s, 3H), 4.15(q, 2H), 5.27(s, 2H), 7.21–7.38(m, 5H) |
| 638 | 1.20(d, 6H), 1.59(s, 6H), 1.91(s, 3H), 4.9–5.1(m, 1H), 5.25(s, 2H), 7.2–7.4(m, 5H) |
| 645 | 1.58(s, 6H), 1.90(s, 3H), 5.11(s, 2H), 5.25(s, 2H), 7.20–7.38(m, 10H) |
| 650 | 0.93(t, 3H), 1.53(s, 3H), 1.77–1.91(m, 1H), 1.93(s, 3H), 2.21–2.36(m, 1H), 5.22, 5.25(ABq, 2H), 7.22–7.39(m, 5H) |
| 651 | 0.91(t, 3H), 1.48(s, 3H), 1.75–1.89(m, 1H), 1.92(s, 3H), 2.12–2.27(m, 1H), 3.69(s, 3H), 5.22, 5.25(ABq, 2H), 7.23–7.38(m, 5H) |
| 683 | 1.57(s, 6H), 1.88(d, 3H), 5.11(s, 2H), 5.28(s, 2H), 7.02–7.16(m, 2H), 7.24–7.33(m, 2H), 7.30(s, 5H) |
| 687 | 1.07(t, 3H), 1.58(s, 6H), 2.15(q, 2H), 5.12(s, 2H), 5.25(s, 2H), 7.2–7.5(m, 10H) |
| 690 | 0.84(t, 3H), 1.5–1.8(m, 8H), 2.15(t, 2H), 5.11(s, 2H), 5.24(s, 2H), 7.1–7.4(m, 10H) |

TABLE 8

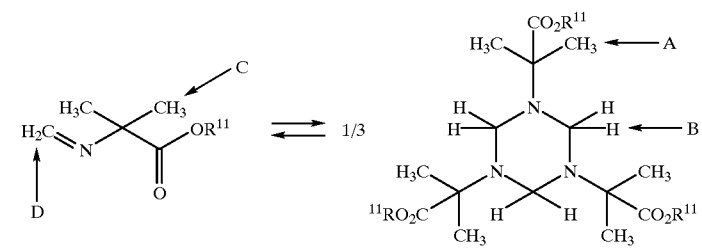

| Compd. No. | ¹H-NMR(300 MHz) δ (ppm) Solvent CDCl₃ TMS = 0 ppm |
|---|---|
| 2-10 | 1.34(s, 6H), 3.67(s, 2H), 5.06(s, 2H), 7.25–7.39(m, 5H) (trimer) |
| 2-15 | 0.80–0.92(m, 3H), 1.28–1.42(m, 3H); 1.68–1.90(m, 2H), 3.60–3.76(m, 3H+B), 7.42, 7.48(ABq, D) |

Next, several embodiments of formulations using the compound of this invention will be shown. In the following formulations, all "parts" are by weight.

Formulation Example 1 (Emulsion Concentrate)

| Compound No. 1 | 20 parts |
| Xylene | 63 parts |
| Calcium dodecylbenzenesulfonate | 7 parts |
| Polyoxyethylenestyryl phenyl ether | 5 parts |
| Dimethylformamide | 5 parts |

The above materials were uniformly mixed and dissolved, to obtain 100 parts of emulsion concentrate.

Formulation Example 2 (Wettable Powder)

| Compound No. 1 | 20 parts |
| Kaolinite | 70 parts |
| Calcium lignosulfonate | 7 parts |
| Condensate of alkylnaphthalenesulfonic acid | 3 parts |

The above materials were mixed and crushed using a jet mill, to obtain 100 parts of wettable powder.

Formulation Example 3 (Suspension Concentrate)

| Compound No. 1 | 20 parts |
| Sodium di(2-ethylhexyl)sulfosuccinate | 2 parts |
| Polyoxyethylene nonylphenylether | 2 parts |
| Defoaming agent | 0.5 parts |
| Propylene glycol | 5 parts |
| Xanthan gum | 0.01 parts |
| Water | 70.49 parts |

The above materials were crushed and uniformly mixed by using a wet-type ball mill, to obtain 100 parts of suspension concentrate.

Formulation Example 4 (Granule)

| Compound No. 1 | 1 parts |
| Sodium di(2-ethylhexyl)sulfosuccinate | 2 parts |
| Bentonite | 30 parts |
| Talc | 67 parts |

The above materials were sufficiently mixed, kneaded with an addition of a suitable amount of water and granulated by a granulator to obtain 100 parts of a granule.

The herbicidal effects of the compound of this invention will be explained below according to the test examples.

Test Example 1 (Paddy Field Soil Application)

Paddy field soil was filled in 500 cm$^2$ wagner pots, suitable amounts of water and chemical fertilizers were added thereto, and kneaded to convert it to a paddy field state. A stock of paddy field rice plant (variety; Koshihikari) comprising a pair of two seedlings that had been grown in advance in a greenhouse to a stage of two leaves, were transplanted in each pot in a population of one stock per pot. Further, in each pot, there were sown predetermined amounts of seeds of *Echinochloa crus-galli, Monochoria vaginalis, Lindernia procumbens* and *Scirpus juncoides*, respectively, and water was filled to a depth of 3 cm.

On the next day, wettable powders were prepared using the compounds shown in Table 9 below according to Formulation Example 2, and they were diluted with a suitable amount of water so that they contained active ingredients in an amount of 50 g/ha. They were applied by dropping with a pipette.

After 21 days from the application with the chemicals, herbicidal effects on each weed and phytotoxicity on paddy field rice plants were evaluated according to the following criteria. The results obtained are shown in Table 9 below.

| | Evaluation criteria (11 ranks) | |
| --- | --- | --- |
| Score | Herbicidal effects: Ratio of killed weeds compared to the control (%) | Phytotoxicity to crop: Ratio of injured plants compared to the control (%) |
| 0 | 0 | 0 |
| 1 | Above 0 to 10 | Above 0 to 10 |
| 2 | Above 10 to 20 | Above 10 to 20 |
| 3 | Above 20 to 30 | Above 20 to 30 |
| 4 | Above 30 to 40 | Above 30 to 40 |
| 5 | Above 40 to 50 | Above 40 to 50 |
| 6 | Above 50 to 60 | Above 50 to 60 |
| 7 | Above 60 to 70 | Above 60 to 70 |
| 8 | Above 70 to 80 | Above 70 to 80 |
| 9 | Above 80 to 90 | Above 80 to 90 |
| 10 | Above 90 to 100 (withered) | Above 90 to 100 (withered) |

TABLE 9

| Compd. No. | Active ingredient dose g ai/ha | Herbicidal effects | | | | Phytotoxicity Paddy field rice plant |
| --- | --- | --- | --- | --- | --- | --- |
| | | Weed A | Weed B | Weed C | Weed D | |
| 1 | 50 | 10 | 10 | 10 | 10 | 0 |
| 3 | 50 | 10 | 10 | 10 | 10 | 0 |
| 6 | 50 | 10 | 10 | 10 | 10 | 0 |
| 22 | 50 | 10 | 10 | 10 | 10 | 0 |
| 24 | 50 | 10 | 10 | 10 | 10 | 0 |
| 26 | 50 | 10 | 10 | 10 | 9 | 0 |
| 27 | 50 | 10 | 10 | 10 | 10 | 0 |
| 30 | 50 | 10 | 10 | 10 | 10 | 0 |
| 35 | 50 | 10 | 10 | 10 | 10 | 0 |
| 39 | 50 | 10 | 10 | 10 | 10 | 0 |
| 42 | 50 | 10 | 10 | 10 | 10 | 0 |
| 49 | 50 | 10 | 10 | 10 | 10 | 0 |
| 64 | 50 | 10 | 10 | 10 | 10 | 0 |
| 93 | 50 | 10 | 10 | 10 | 10 | 0 |
| 103 | 50 | 10 | 10 | 10 | 10 | 0 |
| 123 | 50 | 10 | 10 | 10 | 10 | 0 |
| 128 | 50 | 10 | 10 | 10 | 9 | 0 |
| 138 | 50 | 10 | 10 | 10 | 10 | 0 |
| 363 | 50 | 10 | 10 | 10 | 10 | 0 |

In the Tables 9–12, abbreviations of weeds are as follows.
Weed A: *Echinochloa crus-galli*
Weed B: *Monochoria vaginalis*
Weed C: *Lindernia procumbens*
Weed D: *Scripus juncoides*
Weed E: *Digitalia sanguinalis*
Weed F: *Setaria viridis*
Weed G: *Abutilon theophrasti*
Weed H: *Xanthium strumarium*
Weed I: *Polygonum lapathifolium*
Weed J: *Datura stramonium*

Test Example 2 (Paddy Field Foliar Application)

Paddy field soil was filled in 500 cm$^2$ wagner pots, suitable amounts of water and chemical fertilizers were added thereto, and kneaded to convert it to a paddy field state. A stock of paddy field rice plant (variety; Koshihikari) comprising a pair of two seedlings that had been grown in advance in a greenhouse to a stage of two leaves, were transplanted in each pot in a population of one stock per pot. Further, in each pot, there were sown predetermined amounts of seeds of *Echinochloa crus-galli, Monochoria vaginalis, Lindernia procumbens* and *Scirpus juncoides*, respectively, and water was filled to a depth of 3 cm.

After having grown the plants in a greenhouse until *Echinochloa crus-galli* reached a stage of 1.5 leaves, wettable powders were prepared using the compounds shown in Table 10 below according to Formulation Example 2, and they were diluted with a suitable amount of water so that they contained active ingredients in an amount of 100 g/ha. They were applied by dropping with a pipette.

After 21 days from the application with the chemicals, herbicidal effects on each weed and phytotoxicity on paddy field rice plants were evaluated according to the criteria shown in Test Example 1 above. The results obtained are shown in Table 10 below.

TABLE 10

| Compd. No. | Active ingredient dose g ai/ha | Herbicidal effects | | | | Phytotoxicity Paddy field rice plant |
|---|---|---|---|---|---|---|
| | | Weed A | Weed B | Weed C | Weed D | |
| 1 | 100 | 10 | 10 | 10 | 10 | 0 |
| 3 | 100 | 10 | 10 | 10 | 10 | 0 |
| 6 | 100 | 10 | 10 | 10 | 10 | 0 |
| 22 | 100 | 10 | 10 | 10 | 9 | 0 |
| 24 | 100 | 10 | 10 | 10 | 10 | 0 |
| 26 | 100 | 10 | 10 | 10 | 8 | 0 |
| 27 | 100 | 10 | 10 | 10 | 9 | 0 |
| 30 | 100 | 10 | 10 | 10 | 9 | 0 |
| 35 | 100 | 10 | 10 | 10 | 10 | 0 |
| 39 | 100 | 10 | 10 | 10 | 9 | 0 |
| 42 | 100 | 10 | 10 | 10 | 10 | 0 |
| 49 | 100 | 10 | 10 | 10 | 10 | 0 |
| 64 | 100 | 10 | 10 | 10 | 10 | 0 |
| 93 | 100 | 10 | 10 | 10 | 10 | 0 |
| 103 | 100 | 10 | 10 | 10 | 10 | 0 |
| 123 | 100 | 10 | 10 | 10 | 10 | 0 |
| 128 | 100 | 10 | 10 | 10 | 8 | 0 |
| 135 | 100 | 10 | 10 | 10 | 10 | 0 |
| 363 | 100 | 10 | 10 | 10 | 10 | 0 |

Test Example 3 (Upland Soil Application)

Upland soil was filled in 900 cm² plastic pots, in which there were sown predetermined amount of seeds of *Echinochloa crus-galli, Drigitaria sanguinalis, Setaria viridis, Abutilon theophrasti, Xanthium strumarium, Polygonum lapathifolium* and *Datura stramonium*, respectively, and soil was placed thereon to a thickness of 1 cm.

On the day after sowing, wettable powders were prepared using the compounds shown in Table 11 below according to Formulation Example 2, and they were diluted with a suitable amount of water so that they contained active ingredients in an amount of 1 kg/ha. They were sprayed uniformly over the surface of soil.

After 21 days from the application with the chemicals, herbicidal effects on each weed were evaluated according to the criteria shown in Test Example 1 above. The results obtained are shown in Table 11 below.

TABLE 11

| Compd. No. | Active ingredient dose g ai/ha | Herbicidal effects | | | | | | |
|---|---|---|---|---|---|---|---|---|
| | | Weed A | Weed E | Weed F | Weed G | Weed H | Weed I | Weed J |
| 1 | 1000 | 10 | 10 | 10 | 10 | 8 | 9 | 8 |
| 3 | 1000 | 10 | 10 | 10 | 10 | 8 | 9 | 7 |
| 6 | 1000 | 10 | 10 | 10 | 10 | 9 | 10 | 9 |
| 24 | 1000 | 10 | 10 | 10 | 10 | 9 | 10 | 9 |
| 35 | 1000 | 10 | 10 | 10 | 10 | 9 | 10 | 9 |
| 42 | 1000 | 10 | 10 | 10 | 10 | 9 | 10 | 9 |
| 49 | 1000 | 10 | I0 | 10 | 10 | 8 | 9 | 8 |
| 93 | 1000 | 10 | 10 | 10 | 9 | 7 | 8 | 8 |
| 363 | 1000 | 10 | 10 | 10 | 10 | 9 | 10 | 10 |

Test Example 4 (Upland Foliar Application)

Upland soil was filled in 900 cm² plastic pots, in which there were sown predetermined mined amount of seeds of *Echinochloa crus-galli, Drigitaria sanguinalis, Setaria viridis, Abutilon theophrasti, Xanthium strumarium, Polygonum lapathifolium* and *Datura stramonium*, respectively, and soil was placed thereon to a thickness of 1 cm.

After having grown the plants in a greenhouse until each plant reached a stage of from 2 to 4 leaves, wettable powders were prepared using the compounds shown in Table 12 below according to Formulation Example 2, and they were diluted with a suitable amount of water so that they contained active ingredients in an amount of 1 kg/ha. They were sprayed uniformly over the surface of leaves.

After 21 days from the application with the chemicals, herbicidal effects on each weed were evaluated according to the criteria shown in Test Example 1 above. The results obtained are shown in Table 12 below.

TABLE 12

| Compd. No. | Active ingredient dose g ai/ha | Herbicidal effects | | | | | | |
|---|---|---|---|---|---|---|---|---|
| | | Weed A | Weed E | Weed F | Weed G | Weed H | Weed I | Weed J |
| 1 | 1000 | 10 | 10 | 10 | 10 | 9 | 9 | 9 |
| 3 | 1000 | 10 | 10 | 10 | 10 | 9 | 10 | 8 |
| 6 | 1000 | 10 | 10 | 10 | 10 | 9 | 10 | 10 |
| 24 | 1000 | 10 | 10 | 10 | 10 | 9 | 10 | 10 |
| 35 | 1000 | 10 | 10 | 10 | 10 | 9 | 10 | 10 |
| 42 | 1000 | 10 | 10 | 10 | 10 | 9 | 10 | 10 |
| 49 | 1000 | 10 | 10 | 10 | 10 | 9 | 10 | 9 |
| 93 | 1000 | 10 | 10 | 10 | 10 | 8 | 10 | 9 |
| 363 | 1000 | 10 | 10 | 10 | 10 | 9 | 10 | 8 |

What is claimed is:

1. A 1,3-oxazin-4-one derivative represented by the formula (I):

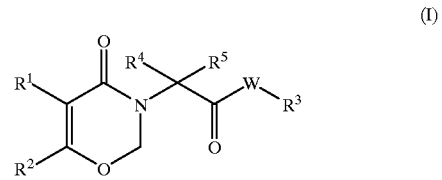

(I)

in which $R^1$ represents a phenyl group which may be substituted; $R^2$ represents a hydrogen atom or a lower alkyl group; R³ represents a hydrogen atom, a lower alkyl group, an aralkyl group selected from the group consisting of benzyl, 1-phenylethyl, 2-phenylethyl-1-methyl-1-phenylethyl 1-methyl-2-phenylethyl, 1-ethyl-2-phenylethyl, and 3-phenylpropyl or a phenyl group which may be substituted; R⁴ and R⁵ each independently represent a lower alkyl group; and W represents an oxygen atom or a group represented by the formula —N(R⁶)— in which R⁶ represents a hydrogen atom, a lower alkyl group, a lower alkenyl group or a lower alkynyl group, and wherein phenyl may be substituted in R¹ or R³ with one or more of a halogen atom, a hydroxy group, a lower alkyl group, a lower alkoxy group, a phenoxy group, a lower alkylthio group, a lower alkyl sulfonyl group, a lower haloalkyl group, a lower haloalkoxy group, an alkoxycarbonyl group, an alkoxycarbonylalkoxy group, an acyl group, a cyano group, and a nitro group.

2. The compound according to claim 1, wherein R¹ is a phenyl group, a 2-fluorophenyl group, a 2-chlorophenyl group or a 2-methylphenyl group.

3. The compound according to claim 1, wherein R² is a hydrogen atom, a methyl group or an ethyl group.

4. The compound according to claim 1, wherein R³ is a phenyl group; a phenyl group substituted at the 3-position by one substituent selected from the group consisting of a halogen atom, a lower-alkyl group, a lower alkoxy group, a phenoxy group, a lower haloalkyl group and a lower haloalkoxy group; or a phenyl group substituted at the 2- and 5-positions or 3- and 5-positions by two substituents selected from the group consisting of a halogen atom, a lower alkyl group, a lower alkoxy group, a phenoxy group, a lower haloalkyl group and a lower haloalkoxy group.

5. The compound according to claim 1, wherein R⁴ and R⁵ are each independently a methyl group or an ethyl group.

6. The compound according to claim 1, wherein W is a group represented by the formula —N(R⁶)— in which R⁶ is a hydrogen atom, a lower alkyl group, a lower alkenyl group or a lower alkynyl group.

7. The compound according to claim 1, wherein W is a group represented by the formula —NH— or —N(CH₃)—.

8. A 1,3-oxazin-4-one derivative represented by following formula (I-1):

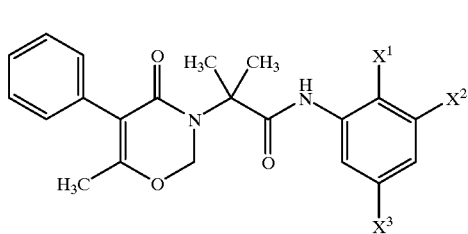

(I-1)

in which X¹, X² and X³ each independently represent a hydrogen atom, a halogen atom, a lower alkyl group, a lower alkoxy group, a phenoxy group, a lower haloalkyl group or a lower haloalkoxy group.

9. The compound according to claim 8, wherein X¹ is a fluorine atom, X² is a hydrogen atom and X³ is a halogen atom, a lower alkyl group, a lower alkoxy group, a phenoxy group, a lower haloalkyl group or a lower haloalkoxy group.

10. The compound according to claim 8, wherein X¹ is a hydrogen atom, X² is a trifluoromethyl group and X³ is a hydrogen atom.

11. An N-methylene amino acid ester derivative represented by the following formula (II):

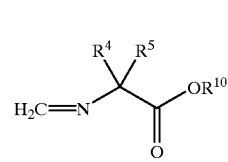

(II)

in which R⁴ and R⁵ each independently represent a lower alkyl group, and R¹⁰ represents a lower alkyl group or an aralkyl group selected from the group consisting of benzyl, 1-phenylethyl, 2-phenylethyl, 1-methyl-1-phenylethyl, 1-methyl-2-phenylethyl, 1-ethyl-2-phenylethyl, and 3-phenylpropyl.

12. A herbicide containing a 1,3-oxazin-4-one derivative represented by the formula (I) of claim 1 as an active ingredient.

13. A herbicidal composition comprising an effective amount of 1,3-oxazin-4-one derivative represented by the formula (I) of claim 1 and an agriculturally and horticulturally acceptable carrier and/or diluent.

14. Herbicidal compositions according to claim 13 which further comprise a second herbicidally active ingredient which is a carbamate derivative or an urea derivative or a haloacetamide derivative or a amide derivative or a dinitrophenyl derivative or a phenoxy derivative or a carboxylic acid derivative or a an organophosphorous compound or a benzonitrile derivative or a diphenylether derivative or a triazine derivative or a sulfonylurea derivative or a diazine derivative.

15. Herbicidal compositions according to claim 14 wherein the second active ingredient is selected from the group consisting of 2,4-D, 2,4-DB, 2,4,5-T, 2,3,6-TBA, Acifluorfen, Alachlor, Atrazin, Benthiocarb, Bensulfuron methyl, Bentazone, Benzofenap, Bifenox, Bromacil, Bromobutide, Bromoxynil, Butachlor, Butamifos, Chlorimuron ethyl, Clopyralid, Chloroproham, Chloroxuron, Chlorbromuron, Chloramben, Chloridazon, Clomeprop, Chlornitrofen, Chlorosulfuron, Chlomethoxyfen, Code number JC-940, Dalapone, Desmedipham, Dicamba, Dichlorprop, Diclofop, Dichlobenil, Dimethametryn, Dimepiperate, Diphenamid, DNOC, Dinoterb, Dinoseb, Dinitramine, Dymron, Diuron, Esprocarb, Fluazifop, Fluometuron, Fluorodifen, Ioxynil, Lenacil, Linuron, Mecoprop, Mefenacet, Metamitron, Metribuzin; Molinate, Monolinuron, MCPB, MCPA, MCPA thioethyl, Naproanilide, Naptalam, Nitralin, Nitrofen, Oxyfluorfen, Pendimethalin, Phenmedipham, Phenothiol, Picloram, Piperophos, Pretilachlor, Prometryn, Propachlor, Propanil, Pyrazolate, Pyrazoxyfen, SAP, Simazine, Simetryn, Swep, Trifluralin, TCA, and Terbacil.

16. Herbicidal compositions according to claim 13 which comprise between 0.1 to 99% (w/w) of active ingredients, preferably between 1 and 80%.

17. Herbicidal compositions according to claim 16 in the form of a wettable powder which comprises 25 to 90% of active ingredient.

18. Herbicidal compositions according to claim 16 in the form of a granule which comprises 1 to 35% of active ingredient.

19. Herbicidal compositions according to claim 16 in the form of an emulsion concentrate which comprises 5 to 30% of active ingredient.

20. Herbicidal compositions according to claim 16 in the form of a suspension concentrate which comprises 5 to 50% of active ingredient.

21. A method for controlling weeds at a locus which comprises applying to locus in need of weed control an effective amount of a composition according to claim 13.

22. A method for controlling the growth of weed at a locus which comprises applying to the locus a composition according to claim 13 wherein the rate of application of the active ingredient is between 1 and 5000 g/ha.

23. A method according to claim 21 wherein the locus is planted or going to be planted with rice.

* * * * *